(12) United States Patent
Kopcho et al.

(10) Patent No.: US 7,193,081 B2
(45) Date of Patent: Mar. 20, 2007

(54) PROCESS FOR PREPARATION OF CYCLIC PRODRUGS OF PMEA AND PMPA

(75) Inventors: Joseph J. Kopcho, San Diego, CA (US); K. Raja Reddy, San Diego, CA (US); Michael C. Matelich, San Diego, CA (US); Bheemarao G. Ugarkar, Escondido, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 15 days.

(21) Appl. No.: 10/436,799

(22) Filed: May 12, 2003

(65) Prior Publication Data

US 2003/0225277 A1 Dec. 4, 2003

Related U.S. Application Data

(60) Provisional application No. 60/380,321, filed on May 13, 2002.

(51) Int. Cl.
C07F 9/6574 (2006.01)
(52) U.S. Cl. .................................. 544/244
(58) Field of Classification Search ........... 544/244
See application file for complete search history.

(56) References Cited

U.S. PATENT DOCUMENTS

| | | | |
|---|---|---|---|
| 3,018,302 A | 1/1962 | Bielefeld et al. | |
| 4,659,825 A | 4/1987 | Holy et al. | |
| 4,724,233 A | 2/1988 | De Clercq et al. | |
| 4,808,716 A | 2/1989 | Holy et al. | |
| 4,952,740 A | 8/1990 | Juge et al. | |
| 5,130,427 A | 7/1992 | Alexander et al. | |
| 5,142,051 A | 8/1992 | Holy et al. | |
| 5,157,027 A | 10/1992 | Biller et al. | |
| 5,514,798 A | 5/1996 | Bischofberger et al. | |
| 5,658,889 A | 8/1997 | Gruber et al. | |
| 5,665,386 A | 9/1997 | Benet et al. | |
| 5,686,629 A | 11/1997 | Bischofberger et al. | |
| 5,716,928 A | 2/1998 | Benet et al. | |
| 5,962,440 A | 10/1999 | Sulsky | |
| 5,962,522 A | 10/1999 | Wacher et al. | |
| 6,004,927 A | 12/1999 | Benet et al. | |
| 6,028,054 A | 2/2000 | Benet et al. | |
| 6,037,335 A | 3/2000 | Takashima et al. | |
| 6,054,587 A | 4/2000 | Reddy et al. | |
| 6,110,903 A | 8/2000 | Kasibhatla et al. | |
| 6,121,234 A | 9/2000 | Benet et al. | |
| 6,180,666 B1 | 1/2001 | Wacher et al. | |
| 6,284,748 B1 | 9/2001 | Dang et al. | |
| 6,294,672 B1 | 9/2001 | Reddy et al. | |
| 6,312,662 B1 | 11/2001 | Erion et al. | |
| 6,399,782 B1 | 6/2002 | Kasibhatla et al. | |
| 6,489,476 B1 | 12/2002 | Dang et al. | |
| 6,752,981 B1 | 6/2004 | Erion et al. | |
| 6,946,115 B2 | 9/2005 | Erion et al. | |
| 2003/0229225 A1 | 12/2003 | Reddy et al. | |
| 2004/0092476 A1 | 5/2004 | Erion et al. | |
| 2004/0192651 A1 | 9/2004 | Boyer et al. | |
| 2005/0282782 A1* | 12/2005 | Martin .................. 544/244 | |
| 2005/0288240 A1 | 12/2005 | Erion et al. | |
| 2006/0030545 A1 | 2/2006 | Cheng et al. | |
| 2006/0046981 A1 | 3/2006 | Shibata | |

FOREIGN PATENT DOCUMENTS

| | | |
|---|---|---|
| EP | 0161955 A1 | 11/1985 |
| EP | 0180276 A1 | 5/1986 |
| EP | 0338372 A2 | 10/1989 |
| EP | 0 481 214 B1 | 9/1991 |
| EP | 0632048 A1 | 1/1995 |
| EP | 0353692 B1 | 10/1995 |
| WO | WO 91/19721 A1 | 12/1991 |
| WO | WO 93/19075 | 9/1993 |

(Continued)

OTHER PUBLICATIONS

Schultz, Bioorganic & Medicinal Chemistry 11, 885 (2003).*

(Continued)

*Primary Examiner*—Mark L. Berch
(74) *Attorney, Agent, or Firm*—Sterne, Kessler, Goldstein & Fox P.L.L.C.

(57) ABSTRACT

The method of preparing compounds of Formula I is described:

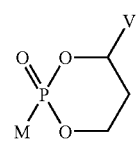

Formula I wherein:
M and V are cis to one another and $MPO_3H_2$ is a phosphonic acid selected from the group consisting of 9-(2-phosphonylmethoxyethyl)adenine, and (R)-9-(2-phosphonylmethoxypropyl)adenine; wherein V is phenyl, optionally substituted with 1–2 substituents selected from a group consisting of fluoro, chloro, and bromo; comprising: coupling a chiral 1-phenylpropane-1,3-diol, wherein the phenyl may be optionally substituted, with $MPOCl_2$ or an N-6 substituted analogue thereof.

Additionally, methods and salt forms are described that enable isolation and purification of the desired isomer.

66 Claims, No Drawings

FOREIGN PATENT DOCUMENTS

| | | |
|---|---|---|
| WO | WO 96/01267 A1 | 1/1996 |
| WO | WO 97/03679 A1 | 2/1997 |
| WO | WO 99/04774 | 2/1999 |
| WO | WO 00/38666 A2 | 7/2000 |
| WO | WO 00/52015 A2 | 9/2000 |

OTHER PUBLICATIONS

Alexander, et al., "Preparation of 9-(2-Phosphonomethoxyethyl)Adenine Esters as Potential Prodrugs," *Collect. Czech. Chem. Commun.*, 59:1853-69 (1994).

Balzarini, et al., "Activity of the (R)-enantiomers of 9(2-phosphonylmethoxypropyl)-adenine and 9(2-phosphonylmethoxypropyl)-2,6-diaminopurine against human immunodeficiency virus in different human cell systems," *Biochem Biophys Res Commun.*, 219(2):337-41 (1996).

Benhamou, et al., "Safety and efficacy of adefovir dipivoxil in patients co-infected with HIV-1 and lamivudine-resistant hepatitis B virus: an open-label pilot study," *Lancet.*, 358(9283):718-23 (2001).

Benzaria, et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," *J. Med. Chem.*, 39:4958-65 (1996).

Bhongle, et al., "Expedient and High-Yield Synthesis of Alkylphosphonyl Dichlorides Under Mild, Neutral Conditions: Reaction of Bis(Trimethylsilyl)Alkyl Phosphonates with Oxalyl Chloride/Dimethylformamide," *Synthetic Comm.*, 17(9):1071-6 (1987).

Bijsterbosch, et al., "Disposition of the acyclic nucleoside phosphonate (S)-9-(3-hydroxy-2-phosphonylmethoxypropyl)adenine," *Antimicrob Agents Chemother*, 42(5):1146-50 (1998).

Brechbuhler, et al., "Die Reaktion von Carbonsauren mit Acetalen des N,N-Dimethylformamids: eine Veresterungsmethode," *Helvetica Chimica Acta.*, 48(187):1746-71 (1965).

Bronson, et al., "Synthesis and Antiviral Activity of Nucleotide Analogs Bearing the (S)—(3-hydroxy-2-phosphonylmethoxy)propyl Moiety Attached to Adenine, Guanine, and Cytosine," *Pharm. Res. Dev.*, 401:88-102 (1989).

Bronson, et al., "Synthesis and Antiviral Activity of Phosphonylmethoxyethyl Derivatives of Purine and Pyrimidine Bases," *Pharm. Res. Dev.*, 401:72-87 (1989).

Campagne, et al., "Synthesis of Mixed Phosphonate Diester Analogues of Dipeptides using BOP or PyBOP Reagents," *Tetrahedron Lett.*, 34(42):6743-4 (1993).

Campbell, "The Synthesis of Phosphonate Esters, and Extension of the Mitsunobu Reation," *J. Org. Chem.*, 57:6331-5 (1992).

Casara, et al., "Synthesis of Acid Stable 5'-o-fluoromethyl Phosphonates of Nucleosides. Evaluation as Inhibitors of Reverse Transcriptase," *Bioorganic & Med. Chem. Lett.*, 2(2):145-8 (1992).

Chu, et al., "A Regiospecific Synthesis of 1-methylamino-6-fluoro-7-(-methylpiperazin-1-yl)-1, 4-dihydro-4-oxoquinoline-3-carboxylic Acid," *J. Het. Chem.*, 22:1033-4 (1985).

Chu, et al., "Chemistry and Antiviral Activities of Acyclonucleosides," *J. Het. Chem.*, 23(2):289-319 (1986).

Coppi, et al., "Lewis Acid Mediated Condensation of Alkenols and Aldehydes. A Selective Synthesis of Tetrahydropyrans and Oxepanes," *J. Org. Chem.*, 53:911-3 (1988).

Cundy, "Clinical Pharmacokinetics of the Antiviral Nucleotide Analogues Cidofovir and Adefovir," *Clin. Pharmacokinet.*, 36(2):127-43 (1999).

De Clercq, et al., "Antiviral activity of phosphonylmethoxyalkyl derivatives of purine and pyrimidines.," *Antiviral Res.* 8(5-6):261-72 (1987).

De Waziers, et al., "Cytochrome P 450 Isoenzymes, Epoxide Hydrolase and Glutathione Transferases in Rat and Human Hepatic and Extrahepatic Tissues," *J. Pharm. Experimental Ther.*, 253(1):387-394 (1990).

Deeks, et al., "The Safety and Efficacy of Adefovir Dipivoxil, a Novel Anti-Human Immunodeficiency Virus (HIV) Therapy, in HIV-Infectedd Adults: A Randomized, Double-Blind, Placebo-Controlled Trial," *J. Infect. Dis.*, 176:1517-23 (1997).

Gao, et al., "Asymmetric Synthesis of Both Enantiomers of Tomoxetine and Fluoxetine. Selective Reduction of 2,3-Epoxycinnamyl Alcohol with Red-A1," *J. Org. Chem.*, 53:4081-4 (1988).

Gilead Press Release, "Gilead Achieves Primary Endpoint in Phase III Study of Adefovir Dipivoxil for Chronic Hepatitis B Virus Infection," (2001).

Harada, et al., "Resolution of 1,3-Alkanediols via Chiral Spiroketals Derived from *t*-Menthone," *Tetrahedron Lett.*, 28(41):4843-6 (1987).

Hatse, et al., "Mechanistic Study on the Cytostatic and Tumor Cell Differentiation-inducing Properties of 9-(2-phosphonylmethoxyethyl)adenine (PMEA, adefovir)-collected Publications," *Verh K. Acad. Geneeskd Belg.*, 62(5):373-84 (2000).

Holy, et al., "Acyclic Nucleotide Analogues: Synthesis, Antiviral Activity and Inhibitory Effects on Some Cellular and Virus-Encoded Enzymes in Vitro," *Antiviral Res.*, 13(6):295-311 (1990).

Inanaga, et al., "A Rapid Esterification by Mixed Anhydride and it's Application to Large-ring Lactonization," *Bull. Chem. Soc. of Japan*, 52(7):1989-93 (1979).

Khamnei, et al., "Neighboring Group Catalysis in the Design of Nucleotide Prodrugs," *J. Med. Chem.*, 39:4109-15 (1996).

Kim, et al., "Synthesis and Biological Activities of Phosphonylalkylpurine Derivatives," *Pharm. Res. Dev.*, 8(5-6):927-931 (1989).

Kobayashi, et al., "Acylation of Active Methylene Compounds via Palladium Complex-Catalyzed Carbonylative Cross-Coupling of Organic Halides," *Tetrahedron Lett.*, 27(39):4745-8 (1986).

Mitsunobu, "The Use of Diethyl Azodicarboxylate and Triphenylphosphine in Synthesis and Transformation of Natural Products," *Synthe.*, 1-28 (1981).

Moriarty, et al., "Diphenyl Methylphosphonate as a Phosphonylation Reagent with High Diastereoselectivity at Phosphorus," *Tetrahedron Lett.*, 38(15):2597-600 (1997).

Mukaiyama, "Chapter 3: The Directed Aldol Reaction," *Org. React.*, 28:203-331 (1982).

Murono, et al., "Prevention and inhibition of nasopharyngeal carcinoma growth by antiviral phosphonated nucleoside analogs," *Cancer Res.*, 61(21):7875-7 (2001).

Naesens, et al., "HPMPC (cidofovir), PMEA (adefovir) and Related Acyclic Nucleoside Phosphonate Analogs: a Review of Their Pharmacology and Clinical Potential in the Treatment of Viral Infections," *Antiviral Chem & Chem.*, 8(1):1-23 (1997).

Naesens, et al., "Therapeutic Potential of HPMPC (Cidofovir), PMEA (Adefovir) and Related Acyclic Nucleoside Phosphonate Analogues as Broad-Spectrum Antiviral Agents," *Nucleosides & Nucleotides*, 16(7-9):983-92 (1997).

Ohashi, et al., "Synthesis of Phosphonosphingoglycolipid Found in Marine Snail Turbo Cornutus," *Tetrahedron Lett.*, 29(10):1189-92 (1988).

Oliyai, et al., "Kinetic Studies of the Degradation of Oxycarbonyloxymethyl Prodrugs of Adefovir and Tenofovir in Solution," *Nucleosides, Nucleotides & Nucleic Acids*, 20(4-7):1295-1298 (2001).

Patois, et al., "Easy Preparation of Alkylphosphonyl Dichlorides," *Lab. Heteroelements Coord.*, 130(4):485-7 (1993).

Phillion, et al., "Synthesis and Reactivity of Diethyl Phosphonomethyltriflate," *Tetrahedron Lett.*, 27(13):1477-80 (1986).

Quast, et al., "Herstellung von Methylphosphonsaure-dichlorid," *Synthesis*, 490 (1974).

Ramachandran, et al., "Efficient General Synthesis of 1,2- and 1,3-Diols in High Enantiomeric Excess via the Intramolecular Asymmetric Reduction of the Corresponding Ketoalkyl Diisopinocampheylborinate Intermediates," *Tetrahedron Lett.*, 38(5):761-4 (1997).

Sakamoto, et al., "The Palladium-Catalyzed Arylation of 4*H*-1,3-Dioxin," *Tetrahedron Lett.*, 33:(45)6845-8 (1992).

Schultze, et al., "Practical Synthesis of the anti-HIV Drug, PMPA," *Tetrahedron Lett.*, 39:1853-6 (1998).

Serafinowska, et al., "Synthesis and in Vivo Evaluation of Prodrugs of 9-[2-)Phosphonomethoxy)ethoxy]adenine," *J. Med. Chem.*, 38:1372-9 (1995).

Shaw, et al., "Pharmacokinextics and Metabolism of Selected Prodrugs of PMEA in Rats," *Drug Metabolism Dis.*, 25(3):362-366 (1997).

Starrett, et al., "Synthesis, oral bioavailability determination, and in vitro evaluation of prodrugs of the antiviral agent 9-[2-(phosphonomethoxy)ethyl]adenine (PMEA)," *J Med Chem.*, 37(12):1857-64 (1994).

Still, et al., "Direct Synthesis of Z-Unsaturated Esters. A Useful Modification of the Horner-Emmons Olefination," *Tetrahedron Lett.*, 24(41):4405-8 (1983).

Stowell, et al., "The Mild Preparation of Synthetically Useful Phosphonic Dichlorides: Application to the Synthesis of Cyclic Phosphonic Diesters and Diamides," *Tetrahedron Lett.*, 31(23):3261-2 (1990).

Tawfik, et al., "1,8-Diazabicyclo[5.4.0]undecene Mediated Transesterification of p-Nitrophenyl Phosphonates: A Novel Route to Phosphono Esters," *Synthesis*, 968-72 (1993).

Turner, "A General Approach to the Synthesis of 1,6-, 1,7-, and 1,8-Naphthyridines," *J. Org. Chem.*, 55:4744-50 (1990).

Turner, et al., "Acylation of Ester Enolates by N-Methoxy-N-methylamides: An Effective Synthesis of β-Keto Ester," *J. Org. Chem.*, 54:4229-31 (1989).

Wacher, et al., "Active Secretion and Enterocytic Drug Metabolism Barriers to Drug Absorption," *Adv. Drug Del. Rev.*, 46:89-102 (2001).

Yamamoto, et al., "Synthesis of Pyridine N-Oxide-SbCl5 Complexes and Their Intrmolecular and Oxygen-Transfer Reaction," *Tetrahedron Lett.*, 37:1871-3 (1981).

Schultz, Carsten "Prodrugs of Biologically Active Phosphate Esters" Bioorganic & Medicinal Chemistry. 2003, vol. 11, pp. 885-898.

Amin, D., et al., "1-Hydroxy-3-(methylopentylamino)-propylidene-1,1-bisphosphonic Acid as a Potent Inhibitor of Squalene Synthase," *Arzneim.-Forsch/Drug Res. 46*:759-762, Blackwell Publishing, Inc. (1996).

Atiq, O., et al., "Treatment of Unresectable Primary Liver Cancer with Intrahepatic Fluorodeoxyuridine and Mitomycin C Through an Implantable Pump," *Cancer 69*:920-924, John Wiley and Sons, Inc. (1992).

Auberson, Y., et al., "N-Phosphonoalkyl-5-Aminomethylquinoxaline-2,3-Diones: In Vivo Active AMPA and NMDA-(Glycine) Antagonists," *Bioorg. Med. Chem. Lett. 9*:249-254, Elsevier Science Ltd. (1999).

Balthazor, T. and Grabiak, R.C., "Nickel-Catalyzed Arbuzov Reaction: Mechanistic Observations," *J. Org. Chem. 45*:5425-5426, American Chemical Society (1980).

Beaucage, S.L. and Iyer, R.P., "The Synthesis of Modified Oligonucleotides by the Phosphoramidite Approach and Their Applications," *Tetrahedron 49*:6123-6194, Pergamon Press Ltd. (1993).

Berry, M.N. and Friend, D.S., "High-Yield Preparation of Isolated Rat Liver Parenchymal Cells. A Biochemical and Fine Structural Study," *J. Cell Biol. 43*:506-520, Rockefeller University Press (1969).

Bespalov, A., et al., "Prolongation of morphine analgesia by competitive NMDA receptor antagonist D-CPPene (SDZ EAA 494) in rats," *Eur. J. Pharmacol. 351*:299-305, Elsevier Science B.V. (1998).

Bhongle, N.N., et al., "Expedient and High-Yield Synthesis of Alkylphosphonyl Dichlorides Under Mild, Neutral Conditions: Reaction of Bis(Trimethylsilyl) Alkyl Phosphonates with Oxalyl Chloride/Dimethylformamide," *Synthetic Comm. 17*:1071-1076, Marcel Dekker, Inc. (1987).

Bird, J., et al., "Synthesis of Novel *N*-Phosphonoalkyl Dipeptide Inhibitors of Human Collagenase," *J. Med. Chem. 37*:158-169, American Chemical Society (1994).

Borch, R.F. and Millard, J.A., "The Mechanism of Activation of 4-Hydroxycyclophosphamide," *J. Med. Chem. 30*:427-431, American Chemical Society (1987).

Brill, T. and Landon, S.J., "Arbuzov-like Dealkylation Reactions of Transition-Metal-Phosphite Complexes," *Chem. Rev. 84*:577-585, American Chemical Society (1984).

Bronson, J.J., et al., "Synthesis and Antiviral Activity of Phosphonylmethoxyethyl Derivatives of Purine and Pyrimidine Bases," in *Nucleotide Analogues as Antiviral Agents, ACS Symposium Series 401*, American Chemical Society (1989).

Bronson, J.J., et al., "Synthesis and Antiviral of Nucleotide Analogues Bearing the (S)-(3-Hydroxy-2-phosphonylmethoxy)propyl Moiety Attached to Adenine, Guanine, and Cytosine," in *Nucleotide Analogues as Antiviral Agents, ACS Symposium Series 401*, American Chemical Society (1989).

Casteel, D. and Perl, S.P., "Steric and Electronic Effects in the Aryl Phosphate to Arylphosphonate Rearrangement," *Synthesis* (9):691-693, Georg Thieme Verlag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," *Cancer Res. 55*:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res. 56*:1331-1340, The American Association for Cancer Research (1996).

Cooper, D.B., et al., "Use of Carbohydrate Derivatives for Studies of Phosphorus Stereo-chemistry. Part II. Synthesis and Configurational Assignments of 1,-3,2-Oxathiaphosphorinan-2-ones and 1,3,2-Dioxaphosphorinan-2-thiones," *J. Chem. Soc. Perkin I* 3/2422:1049-1052, Royal Society of Chemistry (1974).

Cundy, K.C., et al., "Oral Formulations of Adefovir Dipivoxil: in Vitro Dissolution and in Vivo Bioavailability in Dogs," *J. Pharm. Sci. 86*:1334-1338, American Chemical Society (1997).

Dearfield, K., et al., "Analysis of the genotoxicity of nine acrylate/methacrylate compounds in L5178Y mouse lymphoma cells," *Mutagenesis 4*:381-393, Oxford University Press (1989).

De Clercq, E., et al., "A novel selective broad-spectrum anti-DNA virus agent," *Nature 323*:464-467, Nature Publishing Group (1986).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun. 204*:407-412, Academic Press, Inc. (1994).

De Lombaert, S., et al., "*N*-Phosphomomethyl Dipeptides and Their Phosphonate Prodrugs a New Generation of Neutral Endopeptidase (NEP, EC 3.4.24.11) Inhibitors," *J. Med. Chem. 37*:498-511, American Chemical Society (1994).

Desos, P., et al., "Structure-Activity Relationships in a Series of 2(1*H*)-Quinolones Bearing Different Acidic Function in the 3-Position: 6,7-Dichloro-2(1*H*)-oxoquinoline-3-phosphonic Acid, a New Potent and Selective AMPA/Kainate Antagonists with Neuroprotective Properties," *J. Med. Chem. 39*:197-206, American Chemical Society (1996).

Dickson, J.K., et al., "Orally Active Squalene Synthase Inhibitors: Bis((acyloxy)alkyl) Prodrugs of the α-Phosphonosulfonic Acid Moiety," *J. Med. Chem. 39*:661-664, American Chemical Society (1996).

Edmundson, R.S., et al., "Cyclic Organophosphorous Compounds. Part 23. Configurational Assignments in the 4-Phenyl-1,3,2λ-dioxaphosphorinane Series. X-Ray Molecular Structure of cis-2-Benzylamino-4-phenyl-1,3,2-dioxaphosphorinane 2-Oxide," *J. Chem. Research (S)*, 122-123, Science Reviews Ltd. (1989).

Enriquez, P., et al., "Conjugation of Adenine Arabinoside 5'-Monophosphate to Arabinogalactan: Synthesis, Characterization, and Antiviral Activity," *Bioconjugate Chem. 6*:195-202, American Chemical Society (1995).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc. 126*:5154-5163, American Chemical Society (Apr. 2004).

Erion, M., et al., "HepDirect™ Prodrugs: A Novel Strategy for Targeting Drugs to the Liver," *Hepatology 36*:301A, AASLD Abstract No. 551, John Wiley & Sons, Inc. (2002).

Erion, M., et al., "Liver-Targeted Drug Delivery Using HepDirect Prodrugs" *J. Pharmacol. Exper. Ther. 312*:554-560, American Society for Pharmacology and Experimental Therapeutics (Feb. 2005).

Erion, M., "Liver-Targeted Nucleoside Prodrugs," presented at the *Gordon Research Conference: Purines, Pyrimidines and Related Substances*, Newport, RI (Jun.-Jul. 2003).

Evans, D.A., et al., "New Procedure for the Direct Generation of Titanium Enolates. Diasteroselective Bond Constructions with Representative Electrophiles," *J. Am. Chem. Soc. 112*:8215-8216, American Chemical Society (1998).

Evans, D.A., et al., "Stereoselective Aldol Reactions of Cholrotitanium Enolates. An Efficient Method of the Assemblage of Polypropionate-Related Synthons," *J. Am. Chem. Soc. 113*:1047, American Chemical Society (1991).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett. 36*:655-658, Elsevier Science Ltd. (1995).

Farquhar, D., et al., "Biologically Reversible Phosphate-Protective Groups," *J. Pharm. Sci. 72*:324-325, American Chemical Society (1983).

Farquhar, D. and Smith, R., "Synthesis and Biological Evaulation of 9-[5'-(2-Oxo-1,3,2-oxazaphosphorinan-2-yl)- β -D-arabinosyl]adenine and 9-[5-(2-Oxo-1,3,2-dioxazaphosphorinan-2-yl)- β -D-arabinosyl]adenine: Potential Neutral Precursors of 9-[ β -D-Arabinofuranosy]adenine 5'-Monophosphate," *J. Med. Chem. 28*:1358-1361, American Chemical Society (1985).

Farquhar, D., et al., "5'-4-(Pivaloyloxy)-1,3,2-dioxaphosphorinan-2-yl]-2'-deoxy-5-fluorouridine: A Membrane-Permeating Prodrug of 5-Fluoro-2'-deoxyuridylic Acid (FdUMP)," *J. Med. Chem. 38*:488-495, American Chemical Society (1995).

Farquhar, D., et al., "Synthesis and Antitumor Evaluation of Bis[(pivaloyloxy) methyl] 2'-Deoxy-5-fluorouridine 5'-Monophosphate (FdUMP): A Strategy to Introduce Nucleotides into Cells," *J. Med. Chem. 37*:3902-3909, American Chemical Society (1994).

Farquhar, D., et al., "Synthesis and Biological Evaluation of Neutral Derivatives of 5-Fluoro-2'-deoxyuridine 5'-Phosphate," *J. Med. Chem. 26*:1153-1158, American Chemical Society (1983).

Fiume, L., et al., "Inhibition of Hepatitis B Virus Replication by Vidarabine Monophosphate Conjugated with Lactosaminated Serum Albumin," *The Lancet 2*:13-15, The Lancet Publishing Group (1988).

Freed, J.J., et al., "Evidence for Acyloxymethyl Esters of Pyrimidine, 5'-Deoxyribonucleotides as Extracellular Sources of Active 5'-Deoxyribonucleotides in Cultured Cells," *Biochem. Pharm. 38*:3193-3198, Elsevier Inc. (1989).

Friis, G.J. and Bundgaard, H., "Prodrugs of phosphates and phosphonates: Novel lipophilic α-acyloxyalkyl ester derivatives of phosphate- or phosphonate containing drugs masking the negative charges of these groups," *Euro. J. Pharm. Sci.* 449-59, Elsevier Science B.V. (1996).

Furegati, S., et al., "Sterochemistry of the Inhibition of α-Chymotrypsin with Optically Active cis-Decaline-Type Organophosphates: $^{31}$P-NMR Studies," *Helvetica Chimica Acta 81*:1127-1138, Wiley-VCH Verlag GmbH & Co. KGaA (1998).

Groen, A.K., et al., "Intracellular Compartmentation and Control of Alanine Metabolism in Rat Liver Parencymal Cells," *Eur. J. Biochem. 122*:87-93, The Federation of European Biochemical Societies and Blackwell Publishing (1982).

Guida, W.C., et al., "Structure-Based Design of Inhibitors of Purine Nucleoside Phosphorylase. 4. A Study of Phosphate Mimics," *J. Med. Chem. 37*:1109-1114, American Chemical Society (1994).

He, K., et al., "Inactivation of Cytochrome P450 3A4 by Bergamottin, a Component of Grapefruit Juice," *Chem. Res. Toxicol. 11*:252-259, American Chemical Society (1998).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," *Chemical Abstracts* 89(17), Chemical Abstracts Service (1978).

Hirayama, N., et al., "Structure and conformation of a novel inhibitor of angiotensin I converting enzyme—a tripeptide containing phosphonic acid," *Int. J. Pept. Protein Res. 38*:20-24, Blackwell Publishing (1991).

Hong, Z. and Lin, C.-C., "Clinical Update of Remofovir (Hepavir B): a Liver-targeting Prodrug of PMEA for the Treatment of Hepatitis B," Presented at the *SRI-Antiviral Drug Discovery & Development Summit*, Mar. 30, 2004.

Hong, Z., "Hepavir B: a Safer and Liver-Targeting Prodrug of PMEA," Presented at the *SRI-Antiviral Drug Discovery & Development Summit*, Ribopharm Inc., Mar. 27, 2003.

Hunston, R., et al., "Synthesis and Biological Properties of Some Cyclic Phosphotriesters Derived from 2'-Deoxy-5-fluorouridine," *J. Med. Chem. 27*:440-444, American Chemical Society (1984).

Jones, S. and Selitsianos, D., "A Simple and Effective Method for Phosphoryl Transfer Using $TiCl_4$ Catalysis" *Org. Lett. 4*:3671-3673, American Chemical Society (published online Sep. 2002).

Keenan, R., et al., "Pathology Reevaluation of the Kociba et al. (1978) Bioassay of 2,3,7,8-TCDD: Implications for Risk Assessment," *J. Tox. Envir. Health 34*:279-296, Hemisphere Publishing Corporation (1991).

Kelley, J.L., et al., "[[(Guaninylalkyl)phosphinico]methyl]phosphonic Acids. Multisubstrate Analogue Inhibitors of Human Erythrocyte Purine Nucleoside Phosphorylase," *J. Med. Chem. 38*:1005-1014, American Chemical Society (1995).

Khorana, H.G., et al., "Cyclic Phosphates. III. Some General Observations on the Formation of Properties of Five-,Six- and Seven-membered Cyclic Phosphate Esters," *J. Am. Chem. Soc. 79*:430-436, American Chemical Society (1957).

Korba, B.A., et al., "Liver-Targeted Antiviral Nucleosides: Enhanced Antiviral Activity of Phosphatidyl-Dideoxyguanosine in Woodchuck Hepatitis Virus Infection *In Vivo,*" *Hepatology 25*:958-963, John Wiley & Sons, Inc. (1996).

Krise, D.P. and Stella, V.J., "Prodrugs of phosphates, phosphonates, and phosphinates," *Adv. Drug. Del. Rev. 19*:287-310, Elsevier Science B.V. (1996).

Kryuchkov, A.A., et al., "Influence of Solvent on the Strength of Cyclic Oxygen-Containing Phosphorus Acids," *Bull. Acad. Sci. USSR, A translation of Izvestiya Akademii Nauk SSSR, Ser. Khim.* 36:1145-1148, Consultants Bureau (1987).

Lau, D., et al., "Safety, Tolerability, Pharmacokinetics and Pharmacodynamics of Remofovir in Chronic HBV Patients in USA and Canada Following Daily Dosing for 28 Days," Presented at the *40th Annual Meeting of EASL*, Paris, France, *J. Hepatology 42(Suppl. 2)*:32, Abstract No. 74, Elsevier Ireland Ltd. (Apr. 2005).

Lefebvre, I., et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," *J. Med. Chem. 38*:3941-3950, American Chemical Society (1995).

Lin, C.-C., et al., "Development of Hepavir B, A Prodrug of PMEA with Excellent Liver-Targeting Properties," *Abstracts of the 39th Annual Meeting of the EASL*, Berlin, Germany, *J. Hepatology 40*:Abstract No. 374, Elsevier Ireland Ltd. (Apr. 2004).

Lin, C.-C., et al., "Pradefovir is a Substrate, but Neither an Inhibitor nor an Inducer for Cytochrome P450," *AASLD Abstracts, Hepatology* 514A:Abstract No. 811, John Wiley & Sons, Inc. (Oct. 2005).

Lin, C.-C., et al., "Remofovir mesylate: a prodrug of PMEA with improved liver-targeting and safety in rats and monkeys," *Antiviral Chem. Chemother. 15*:307-316, International Medical Press (2004).

Lin, C.-C., et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts, *Hepatology 40*:658A, Abstract No. 1141, John Wiley & Sons, Inc. (Oct. 2004).

Lok, A.S.F., et al., "Neurotoxicity associated with adenine arabinoside monophosphate in the treatment of chronic hepatitis B virus infection," *J. Antimicrob. Chemotherap. 14*:93-99, Oxford University Press (1984).

Lu, X. and Zhu, J., "Palladium-Catalyzed Reaction of Aryl Polyfluoroalkanesulfonates with O,O-Dialkyl Phosphonates," *Synthesis (8)*:726-727, Georg Thieme Verlag (1987).

Ludeman, S.M., et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," *J. Med. Chem.* 29:716-727, American Chemical Society (1986).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2',3-40 -didehydrothymidine (d4T)—A New Pro-Nucleotide Approach—" *Bioorg. Med. Chem. Lett.* 7:99-104, Elsevier Science Ltd. (1997).

Meijer, D.K.F., et al., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates," *Tetrahedron Lett.* 22:3375-3376, Pergamon Press Ltd. (1981).

Meyer, R., et al., "2'-O-Acyl-6-thioinosine Cyclic 3',5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkin Trans. 1*, 2345-2353, Royal Society of Chemistry (1992).

Moore, M., et al., "Comparison of mutagenicity results for nine compounds evaluated at the *hgprt* locus in the standard and suspension CHO assays," *Mutagenesis* 6:77-85, Oxford University Press (1991).

Mosbo, J.A. and Verkade, J.G., "Dipole Moment, Nuclear Magnetic Resonance, and Infrared Studies of Phosphorus Configurations and Equalibria in 2-R-2-Oxo-1,3,2-dioxaphosphorinames," *J. Org. Chem.* 42:1549-1555, American Chemical Society (1977).

Mulato, A.S., et al., "Nonsteroidal Anti-Inflammatory Drugs Efficiently Reduce the Transport and Cytotoxicity of Adefovir Mediated by the Human Renal Organic Anion Transporter 1," *J. Pharm. Exp. Ther.* 295:10-15, American Society for Pharmacology and Experimental Therapeutics (2001).

Murray, G., et al., "Cytochrome P450 CYP3A in human renal cell cancer," *Brit. J. Cancer* 79:1836-1842, Nature Publishing Group (1999).

Murray, G., et al., "Cytochrome P450 Expression is a Common Molecular Event in Soft Tissue Sarcomas," *J. Pathology* 171:49-52, John Wiley & Sons, Ltd. (1993).

Nakayama, K. and Thompson, W.J., "A Highly Enantioselective Synthesis of Phosphate Triesters," *J. Am. Chem. Soc.* 112:6936-6942, American Chemical Society (1990).

Neidlein, R., et al., "Mild Preparation of 1-Benzyloxyiminoalkylphosphonic Dichlorides: Application to the Synthesis of Cyclic Phosphonic Deisters and Cyclic Monoesters Amides," *Heterocycles* 35:1185-1203, Elsevier Science (1993).

Nifantyev, E.E., et al., "Synthesis and Structure of Some Stable Phospholane-Phospholanes," *Phosphorus, Sulfu Silicon and Related Elements* 113:1-13, Taylor & Francis (1996).

Noble, S. and Goa, K.L., "Adefovir Dipivoxil," *Drugs* 58:479-487, Adis International Ltd. (1999).

Ogg, M., et al., "A reporter gene assay to assess the molecular mechanisms of xenobiotic-dependent induction of the human CYP3A4 gene *in vitro*," *Xenobiotica* 29:269-279, Taylor & Franics Ltd. (1999).

Ozoe, Y., et al., "Actions of cyclic esters, S-esters, and amides of phenyl-and phenylthiophosphonic acids on mammalia and insect GABA-gated chloride channels," *Bioorg. Med. Chem.* 6:73-83, Elsevier Science Ltd. (1998).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833, American Chemical Society (1987).

Pitcher, H.R., "Built-in Bypass," *Nature* 429:39, Nature Publishing Group (May 2004).

Predvoditelev, D.A., et al., "Glycero-2-Hydroxymethylene Phosphates," *J. Org. Chem. USSR, A Translation of Zhur. Org. Khim.* 13:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim.* 17:1156-1165, Plenum Publishing Corporation (1981).

Prisbe, E.J., et al., "Synthesis and Antiherpes Virus Activity of Phosphate and Phosphonate Deriviates of 9-[(1,3-Dihydorxy-2-propoxy)methyl]guanine",*J. Med. Chem.* 29:671-675, American Chemical Society (1986).

Reddy, K.R., et al., "Stereoselective synthesis of nucleoside monophosphate HepDirect™ prodrugs," *Tetrahedron Lett.* 46:4321-4324, Elsevier Ltd. (2005).

Reddy, M.R., et al., "Development of a Quantum Mechanics-Based Free-Energy Perturbation Method: Use in the Calculation of Relative Solvation Free Energies," *J. Am. Chem. Soc.* 126:6224-6225, American Chemical Society (published online Apr. 2004).

Redmore, D., "Phosphorus Derivatives of Nitrogen Heterocycles. 2. Pyridinophosphonic Acid Derivatives," *J. Org. Chem.* 35:4114-4117, American Chemical Society (1970).

Russell, J.W., et al., "Determination of 9-[(2-phosphonylmethoxyl)ethyl]ethyl]adenine in rat urine by high-performance liquid chromatography with fluorescence detection," *J. Chromatogr.* 572:321-326, Elsevier Science Publishers (1991).

Schlachter, S.T., et al., "Anti-Inflammatory/Antiarthritic Ketonic Bisphosphonic Acid Esters," *Bioorg. Med. Chem. Lett.* 8:1093-1096, Elsevier Science Ltd. (1998).

Shaw, J.-P. and Cundy, K.C., "Biological Screens of PMEA Prodrugs," *Pharm. Res.* 10:S-294, Klower Academic Publishers B.V., Abstract No. PDD 7480 (1993).

Shih, Y.-E., et al., "Preparation and Structures of 2-Dimethylamino-4-phenyl-1,3,2-dioxaphosphorinane-2-oxides," *Bull. Inst. Chem. Acad. Sin.* 41:9-16, Academia Sinica, Nankang, Taipei, Taiwan (1994).

Sullivan-Bolyai, J., et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, *Hepatology* 78A:Abstract No. LB 07, John Wiley & Sons, Inc. (Oct. 2005).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. 1*, 1239-1245, Royal Society of Chemistry (1993).

Van Poelje, P., et al., "MB6866 (Hepavir B), A HepDirect™ Prodrug of Adefovir: Mechanism of Activation and Liver Targeting," AASLD Abstracts, *Hepatology* 706A:Abstract No. 1143, John Wiley & Sons, Inc. (Oct. 2003).

Venook, A., "Treatment of Hepatocellular Carcinoma: Too Many Options?," *J. Clin. Oncol.* 12:1323-1334, American Society of Clinical Oncology (1994).

Vo-Quang, Y., et al., "(1-Amino-2-propenyl)phosphonic Acid, an Inhibitor of Alanine Racemase and D-Alanine:D-Alanine Ligase," *J. Med. Chem.* 29:579-581, American Chemical Society (1986).

Wagner, A., et al., "Direct Conversion of Tetrahydropyranylated Alcohols to the Corresponding Bromides," *Tetra. Lett.* 30:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society (1998).

Walsh, E., et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm.* 45:1685-1694, Pergamon Press Ltd. (1993).

Weibel, M., et al., "Potentiating Effect of {2-[2-[(2-Amino-1,6-Dihydro-6-Oxo-9H-Purin-9-yl)Methyl]-Phenyl] Ethenyl}-Phosphonic Acid (MDL 74,428), A Potent Inhibitor of Purine Nucleoside Phosphorylase, on the Antiretroviral Activities of 2',3'-Dideoxyinosine Combined to Ribavirin in Mice," *Biochem. Pharmacol.* 48:245-252, Elsevier Science Ltd. (1994).

Wileman, T., et al., "Receptor-mediated endocytosis," *Biochem. J.* 232:1-14, Portland Press (1985).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Epx. Ther.* 288:928-937, American Chemical Society for Pharmacology and Experimental Therapeutics (1999).

Zon, G., "Cyclophosphamide Analogues" in *Progress in Medicinal Chemistry*, Ellis, G.P., et al., eds., Elsevier Biomedical Press, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of *cis*-and *trans*-4-Hydroxycyclophosphamide with Aldophosphamide and the Concomitant Partitioning of Aldophosphamide between Irreversible Fragmentation and Reversible Conjugation Pathways," *J. Med. Chem.* 27:466-485, American Chemical Society (1984).

International Search Report for International Application No. PCT/US03/14822, International Search Authority, Alexandria, VA, mailed Feb. 11, 2004.

Office Action for U.S. Appl. No. 10/436,922, Reddy, K., et al., filed May 12, 2003, mailed Jul. 1, 2004.

Office Action for U.S. Appl. No. 10/436,922, Reddy, K., et al., filed May 12, 2003, mailed Sep. 21, 2005.

Erion, M., et al., "HepDirect Prodrugs for Targeting Nucleotide-Based Antiviral Drugs to the Liver," *Current Opinion in Investigational Drugs* 7(2):109-117, The Thomson Corporation (2006).

Office Action for U.S. Appl. No. 10/436,922, Reddy et al., mailed Mar. 17, 2006.

Barluenga, José, et al., "Reduction of 1,3-Diimines. A New and General Method of Synthesis of γ-Diamines, β-Amino Ketones, and Derivatives with Two and Three Chiral Centers," *J. Org. Chem.* 48:2255-2259, American Chemical Society (1983).

Dang, Q., et al., "A New Regio-Defined Synthesis of PMEA," *Nucleosides & Nucleotides* 17/8: 1445-1451, Marcel Dekker, Inc. (1998).

Dyatkina, Natalja, et al., "Synthesis of the Four Possible Stereoisomeric 5'-Nor Carbocyclic Nucleosides from One Common Enantiomerically Pure Starting Material," *Tetrahedron Letters* 35/13: 1961-1994, Elsevier Science Ltd. (1994).

Li, Yuan, et al., "Synthesis of D-arabinofuranosides Using Propane-1,3-diyl Phosphate as the Anomeric Leaving Group," *Tetrahedron Letters* 42: 6615-6618 Elsevier Sciences Ltd. (2001).

Martin, John C., et al., "Synthesis and Antiviral Activity of Various Esters of 9-[(1,3-Dihydroxyl-2-propoxy)methyl]guanine," *J. Pharmaceutical Sciences* 76/2: 180-184 American Pharmaceutical Association (1987).

Ten Hoeve, W. and Wynberg, H., "The Design of Resolving Agents. Chiral Cyclic Phosphoric Acids," *J. Org. Chem.* 50: 4508-4514, American Chemical Society (1985).

Office Action for U.S. Appl. No. 11/145,194, Mark D. Erion et al., filed Jun. 3, 2005, mailed Mar. 24, 2006.

\* cited by examiner

PROCESS FOR PREPARATION OF CYCLIC PRODRUGS OF PMEA AND PMPA

RELATED APPLICATIONS

This application claims benefit of U.S. Provisional Application No. 60/380,321 filed May 13, 2002 and which is incorporated by reference herein in its entirely, including figures.

FIELD OF INVENTION

The present invention is directed towards a process of synthesis of substituted six-membered cyclic 1-aryl-1,3-propanyl esters of PMEA and PMPA. More specifically, the invention relates to the process of synthesis of halogen substituted cyclic-1-phenyl-1,3-propanyl esters of PMEA and PMPA that have cis stereochemistry.

BACKGROUND OF THE INVENTION

The following description of the background of the invention is provided to aid in understanding the invention, but is not admitted to be, or to describe, prior art to the invention. All publications are incorporated by reference in their entirety.

9-(2-phosphonylmethoxyethyl)adenine (PMEA), (R)-9-(2-phosphonyl-methoxypropyl)adenine (PMPA) and related analogues (U.S. Pat. No. 4,808,716; U.S. Pat. No. 5,142,051) are phosphonic acids that exhibit antiviral activity, including activity against hepatitis B and HIV (De Clercq et al., *Antiviral Res.* 8: 261–7(1987); Balzarini et al., *Biochem Biophys. Res. Commun.* 219(2): 337–41(1996)). The dipivaloyloxy methylene ester of PMEA ("BisPOM PMEA") is in clinical trials for the treatment of hepatitis B (Benhamou et al., *Lancet* 358(9283): 718–23 (2001)). In addition, some studies have shown that these compounds also show anticancer activity (Murono et al., *Cancer Res.* 61(21): 7875–7 (2001)).

Compounds containing phosphonic acids and their salts are highly charged at physiological pH and therefore frequently exhibit poor oral bioavailability, poor cell penetration and limited tissue distribution (e.g., CNS). In addition, these acids are also commonly associated with several other properties that hinder their use as drugs, including short plasma half-life due to rapid renal clearance, as well as toxicities (e.g., renal, gastrointestinal, etc.) (e.g., Bijsterbosch et al., *Antimicrob Agents Chemother.* 42(5): 1146–50 (1998)). Cyclic phosphonate esters have also been described for PMEA and related analogues. The numbering for these cyclic esters is shown below:

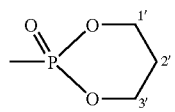

Unsubstituted cyclic 1',3'-propanyl esters of PMEA were prepared but showed no in vivo activity. EP 0 481214 B1 discloses examples of cyclic prodrugs of PMEA wherein the 1' and 3' positions are unsubstituted. The application and a subsequent publication by the inventors (Starrett et al., *J. Med. Chem.* 37:1857–1864 (1994)) further disclose their findings with the compounds, namely that these compounds showed no oral bioavailability and no biological activity.

The compounds were shown to be unstable at low pH, e.g., the cyclic 2',2'-difluoro-1',3'-propane ester is reported to be hydrolytically unstable with rapid generation of the ring-opened monoester.

SUMMARY OF THE INVENTION

The present invention is directed towards a novel process for the synthesis of cyclic 1-aryl-1,3 propanyl phosphonate cyclic esters of PMEA and PMPA with an enhanced d.e. for the cis isomer. In one aspect the process enhances the cis isomers via a coupling method. In another aspect this process for the cis isomers is enhanced by the temperature of the process. In an additional aspect the order of addition of the reactants enhanced the production of the cis isomer. Further aspect is additional enrichment of the desired cis isomer through the addition of an acid and the crystallization of the salt. Another aspect of the process is the enhancement of cis isomer that occurred with the crystallization solvent.

In another aspect, this invention is directed towards a method of making substantially enantiomerically pure cis cyclic esters having S stereochemistry where the V is attached.

One aspect of the invention concerns the method for the preparation of compounds of Formula I:

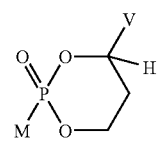

Formula I wherein:

M and V are cis to one another and MPO$_3$H$_2$ is a phosphonic acid selected from the group consisting of 9-(2-phosphonylmethoxyethyl)adenine, and (R)-9-(2-phosphonyl-methoxypropyl)adenine; wherein V is phenyl, optionally substituted with 1–2 substituents selected from a group consisting of fluoro, chloro, and bromo; comprising: coupling a chiral 1-phenylpropane-1,3-diol, wherein the phenyl may be optionally substituted, with MPOCl$_2$ or an N-6 substituted analogue thereof.

Additionally, methods and salt forms are described that enable isolation and purification of the desired isomer.

Definitions

In accordance with the present invention and as used herein, the following terms are defined with the following meanings, unless explicitly stated otherwise.

The term "hexanes" refers to commercially available HPLC reagent solutions which contains approximately 95% hexane, methylcyclopropane, and methylpentane.

The term "dialkyl" refers to a compound containing two alkyl groups. The term "alkyl" refers to saturated aliphatic groups including straight-chain, branched chain and cyclic groups. Suitable alkyl groups include methyl, ethyl, isopropyl, and cyclopropyl.

The term "optionally substituted" or "substituted" includes aryl groups substituted with one to two substituents, independently selected from lower alkyl, lower aryl, and halogens. Preferably these substituents are selected from the group consisting of halogens.

The term "cis" stereochemistry refers to the relationship of the V group and M group positions on the six-membered ring. The formula below shows a cis stereochemistry.

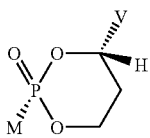

Another cis stereochemistry would have V and M pointing above the plane. The formula below shows this cis stereochemistry.

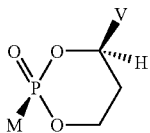

The term "N6-substituted" refers to the substitution at the amine attached at the 6-position of a purine ring system. N6- is generally substituted with a dialkylaminomethylene group wherein $R^1$ groups include but are not limited to C1–C4 acyclic alkyl, C5–C6 cyclic alkyl, benzyl, phenethyl, or $R^1$ groups together form piperdine, morpholine, and pyrrolidine.

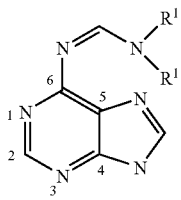

The term "dialkylaminomethyleneimine" refers to functional group or substitution of the following structure:

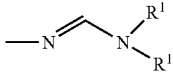

wherein $R^1$ groups include but are not limited to C1–C4 acyclic alkyl, C5–C6 cyclic alkyl, benzyl, phenethyl, or $R^1$ groups together form piperdine, morpholine, and pyrrolidine.

The term "percent enantiomeric excess (% ee)" refers to optical purity. It is obtained by using the following formula:

[R]−[S]×100=% R−% S

[R]+[S]

where [R] is the amount of the R isomer and [S] is the amount of the S isomer. This formula provides the % ee when R is the dominant isomer.

The term "d.e." refers to diastereomeric excess. It is obtained by using the following formula:

$$\frac{[cis]-[trans]}{[cis]+[trans]} \times 100 = \% \ [cis] - \% \ [trans]$$

The term "diastereoisomer" refers to compounds with two or more asymmetric centers having the same substituent groups and undergoing the same types of chemical reactions wherein the diastereoisomers have different physical properties, have substituent groups which occupy different relative positions in space, and may have different biological properties.

The term "racemic" refers to a compound or mixture that is composed of equal amounts of dextrorotatory and levorotatory forms of the same compound and is not optically active.

The term "enantiomer" refers to either of a pair of chemical compounds whose molecular structures have a mirror-image relationship to each other.

The term "acid dissociation constant" ($K_a$) refers to the equilibrium constant for the ionization of an acid, e.g. HA is the formula for a weak acid, then:

$K_a = ([H^+][A^{31}]/[HA])$

The term "halogen" refers to chlorine, bromine, or fluorine.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of Formula I fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds include, for example, anticancer agents, and antiviral agents.

The term "cyclic 1',3'-propane ester", "cyclic 1,3-propane ester", "cyclic 1',3'-propanyl ester", and "cyclic 1,3-propanyl ester" refers to the following:

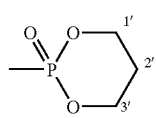

The term "enhancing" refers to increasing or improving a specific property.

The term "enriching" refers to increasing the quantity of a specific isomer produced by a reaction.

The term "pharmaceutically acceptable salt" includes salts of compounds of Formula I derived from the combination of a compound of this invention and an organic or inorganic acid or base, such that they are acceptable to be safely administered to animals. Suitable acids include acetic acid, adipic acid, benzenesulfonic acid, (+)-7,7-dimethyl-2-oxobicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis[3-hydroxy-2-naphthalenecarboxylic acid], phosphoric acid, polygalacturonic acid, stearic acid, succinic acid, sulfuric acid, sulfosalicylic acid, tannic acid, tartaric acid, terephthalic acid, and p-toluenesulfonic acid.

The following well known chemicals are referred to in the specification and the claims. Abbreviations, and common names are also provided.

CH$_2$Cl$_2$; Dichloromethane or methylene chloride
DCM; dichloromethane
(−)-DIP-Cl; (−)-β-Chlorodiisopinocampheylborane
DMAP; 4-dimethylaminopyridine
DMF; Dimethylformamide
HCl; hydrochloric acid
KI; potassium iodide
MgSO$_4$; magnesium sulfate
MTBE; t-butyl methyl ether
NaCl; sodium chloride
NaOH; sodium hydroxide
PyBOP; benzotriazol-1-yloxytripyrrolidinophosphonium hexafluorophosphate
TEA; triethylamine
THF; tetrahydrofuran
TMSCl; chlorotrimethylsilane
bis POM PMEA; bis(pivaloyloxymethyl)-9-(2-phosphonylmethoxyethyl)adenine (Adefovir dipivoxil)

The following well known drugs are referred to in the specification and the claims. Abbreviations and common names are also provided.

PMEA; 9-(2-phosphonylmethoxyethyl)adenine (Adefovir)
(R)-PMPA; (R)-9-(2-phosphonylmethoxypropyl)adenine (Tenofovir)

DETAILED DESCRIPTION OF THE INVENTION

This invention is directed to the discovery that the process for the synthesis of cyclic 1-aryl-1,3-propanyl esters of PMEA and PMPA determined the stereochemistry of the resultant product. Compounds synthesized by the process of the present invention are directed towards the cis stereochemistry of the cyclic esters of PMEA and PMPA. In one aspect of this invention the stereochemistry at the methine carbon which is identified as C1' in the cyclic 1-aryl-1,3-propanyl esters was established through the synthesis of the corresponding chiral 1-aryl-1,3-propane diol e.g., via the chiral reduction of an intermediate ketoacid.

In another aspect it was found that the chirality at the phosphorus of the cyclic phosphonate ring was established during the reaction with the diol. Production of the cis diastereoisomer was dependent on the reaction temperature and the order of addition of the chiral diol and protected parent phosphonic dichloridate to the reaction mixture.

An additional aspect of the invention is the protection of the nitrogen attached to the carbon labeled 6 in the structure below.

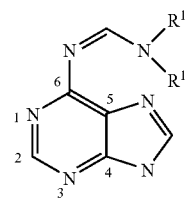

The concentration of the desired cis isomer, wherein cis refers to the geometric relationship between the phosphorus-carbon bond and the carbon-aryl bond of the cyclic phosphonate ring, was enhanced by additional isolation via selective crystallization of the acid salt, which is a further aspect of this invention. Still further enhancement was achieved through recrystallization of the acid addition salt.

The process for the synthesis of cyclic 1-aryl-1,3-propanyl esters of PMEA or PMPA with the desired stereochemistry is via a convergent synthetic sequence starting with adenine and a halogen substituted benzoyl chloride. The final resultant compound contained two stereocenters, (1) the methine carbon which is identified as C1' in the stercoisomeric structures and (2) the phosphorus of the cyclic phosphonate ring. The stereochemistry at the carbon, C1', resulted from the chiral reduction of an intermediate ketoacid and the phosphorus chirality was the result of the diastereoselective coupling of the parent phosphonic acid and the chiral diol. The desired cis isomer, wherein cis refers to the isomeric relationship between the phosphorus-carbon bond and the carbon-phenyl bond of the cyclic phosphonate ring, was isolated via a selective crystallization of the acid salt.

Compounds Prepared by the Invention

The compounds prepared by the invention are substituted 6-membered cyclic 1,3-propane diester prodrugs of PMEA and analogues as represented by Formula I:

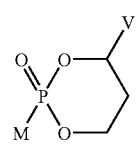

Formula I wherein:

M and V are cis to one another and MPO$_3$H$_2$ is a phosphonic acid selected from the group consisting of 9-(2-phosphonylmethoxyethyl)adenine, and (R)-9-(2-phosphonylmethoxypropyl)adenine;

V is phenyl, optionally substituted with 1–2 substituents selected from a group consisting of F, Cl, and Br;

and pharmaceutically acceptable salts thereof.

Another aspect of the invention is the preparation of the compounds of Formula II

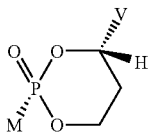

Formula II wherein:

MPO$_3$H$_2$ is a phosphonic acid selected from the group consisting of 9-(2-phosphonylmethoxyethyl)adenine and (R)-9-(2-phosphonylmethoxypropyl)adenine;

V is phenyl, optionally substituted with 1–2 substituents selected from a group consisting of F, Cl, and Br;

and pharmaceutically acceptable salts thereof.

Another aspect is directed to salts of such compounds formed with methanesulfonic acid or succinic acid.

Another aspect is directed to salts formed with methanesulfonic acid.

Another aspect of the invention is the preparation of compounds of Formula II

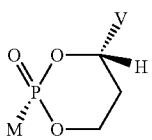

Formula II wherein:

MPO$_3$H$_2$ is a phosphonic acid selected from the group consisting of 9-(2-phosphonylmethoxyethyl)adenine and (R)-9-(2-phosphonylmethoxypropyl)adenine; V is 3-chlorophenyl;

and pharmaceutically acceptable salts thereof.

Another aspect is directed to salts formed with methanesulfonic acid of such compounds.

Another aspect of the invention are the compounds of Formula II

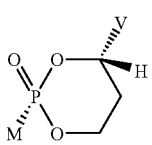

Formula II wherein:

MPO$_3$H$_2$ is a phosphonic acid selected from the group consisting of 9-(2-phosphonylmethoxyethyl)adenine and (R)-9-(2-phosphonylmethoxypropyl)adenine; V is 2-bromophenyl;

and pharmaceutically acceptable salts thereof.

Another aspect is directed to salts formed with methanesulfonic acid of such compounds.

1. Synthesis of 1-(Aryl)-Propane-1,3-Diols:

A variety of synthetic methods are known to prepare 1,3-diols. These suitable methods are divided into two types as following: 1) synthesis of racemic 1-(aryl)-propane-1,3-diol; 2) synthesis of chiral 1-(aryl)-propane-1,3-diol.

1.1 Synthesis of Racemic 1-(Aryl)-Propane-1,3-Diol:

1,3-Dihydroxy compounds can be synthesized by several well known methods in literature. Substituted aromatic aldehydes are utilized to synthesize racemic 1-(aryl)propane-1,3-diol via addition of lithium enolate of alkyl acetate followed by ester reduction (path A) (Turner, *J. Org. Chem.* 55:4744 (1990)). Alternatively, aryl Grignard additions to 1-hydroxy propan-3-al also give 1-(arylsubstitued)propane-1,3-diols (path B). This method will enable conversion of various substituted aryl halides to 1-(arylsubstituted)-1,3-propane diols (Coppi, et al., *J. Org. Chem.* 53:911 (1988)). Aryl halides can also be used to synthesize 1-substituted propane diols by Heck coupling of 1,3-diox-4-ene followed by reduction and hydrolysis (Sakamoto, et al., *Tetrahedron Lett.* 33:6845 (1992)). Pyridyl, quinoline, isoquinoline propan-3-ol derivatives can be oxygenated to 1-substituted-1,3-diols by N-oxide formation followed by rearrangement in acetic anhydride conditions (path C) (Yamamoto, et al., *Tetrahedron* 37:1871 (1981)). A variety of aromatic aldehydes can also be converted to 1-substituted-1,3-diols by vinyl Grignard addition followed by hydroboration reaction (path D).

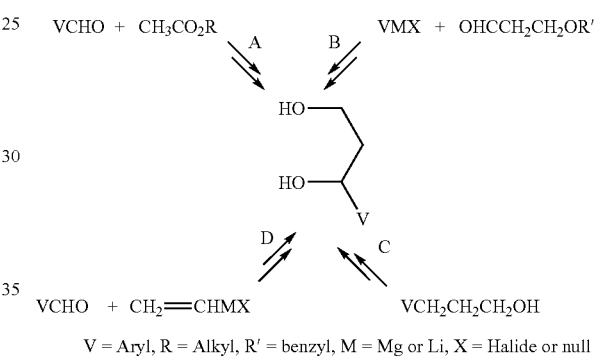

V = Aryl, R = Alkyl, R' = benzyl, M = Mg or Li, X = Halide or null 1.2 Synthesis of Chiral 1-(aryl)-Propane-1,3-Diol:

A variety of known methods for chiral resolution of secondary alcohols via chemical or enzymatic agents may be utilized for preparation of diol enantiomers (Harada, et al., *Tetrahedron Lett.* 28:4843 (1987)). Transition metal catalyzed hydrogenation of substituted 3-aryl-3-oxo propionic acids or esters is an efficient method to prepare R or S isomers of optically pure beta hydroxy acids or esters (*Comprehensive Asymmetric Catalysis*, Jacobsen, E. N., Pfaltz, A., Yamamoto, H. (Eds), Springer, (1999); *Asymmetric Catalysis in Organic Synthesis*, Noyori, R., John Wiley, (1994)). These beta hydroxy acid or ester products can be further reduced to give required chiral 1-(aryl)-propane-1,3-diols. (path A). The β-keto acid or ester substrates for high pressure hydrogenation or hydrogen transfer reactions may be prepared by a variety of methods such as condensation of acetophenone with dimethylcarbonate in the presence of a base (Chu, et al., *J. Het Chem.* 22:1033 (1985)), by ester condensation (Turner, et al., *J. Org. Chem.* 54:4229 (1989)) or from aryl halides (Kobayashi, et al., *Tetrahedron Lett.* 27:4745 (1986)). Alternatively, enantiomerically pure 1,3-diols can be obtained by chiral borane reduction of β-hydroxyethyl aryl ketone derivatives or β-keto acid derivatives (path B) (Ramachandran, et al., *Tetrahedron Lett.* 38:761 (1997)). In another method, commercially available cinnamyl alcohols may be converted to epoxy alcohols under catalytic asymmetric epoxidation conditions. These epoxy alcohols are reduced by Red-Al to result in enantiomerically pure 1,3-diols (path C) (Gao, et al., *J. Org. Chem.* 53:4081 (1980)). Aldol condensation is another well described method for synthesis of the chiral 1,3-oxygenated functionality starting from aromatic aldehydes. (path D) (Mukaiyama, *Org. React.* 28:203 (1982)).

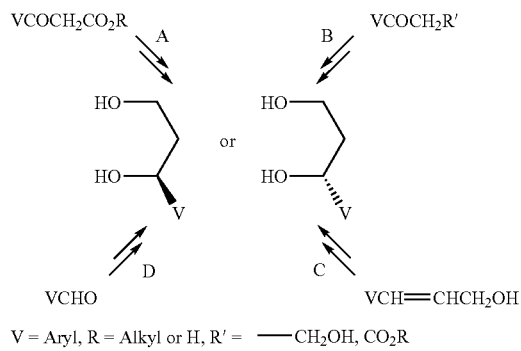

V = Aryl, R = Alkyl or H, R' = ——CH$_2$OH, CO$_2$R

For the purpose of this invention the intermediate ketoacid is prepared from a halogen substituted benzoyl chloride of Formula A wherein the benzoyl chloride may be optionally substituted at any position on the phenyl ring with 1–2 halogens. In a preferred embodiment if R$^2$ is a halogen then R$^3$ must be a hydrogen and if R$^3$ is a halogen then R$^2$ must be a hydrogen. In one embodiment Formula A is 3-chlorobenzoyl chloride and in another embodiment, Formula A is 2-bromobenzoyl chloride. The C1' identifies the carbon that is the methine carbon stereocenter in the final compound prepared by this invention.

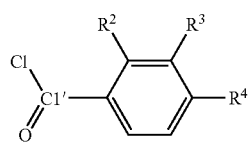

Formula A

The compound of Formula A is reacted with trimethylsilyl acetate and lithium diisopropylamide (generated in situ by reaction of diisopropylamine and n-butyllithium) to obtain the oxo-propanoic acid. The hydroxypropanoic acid is synthesized from the oxo-propanoic acid via reaction with (−)-DIP-Cl and then the hydroxypropanoic acid is reduced to the chiral 1,3-diol, shown in the following Formula B:

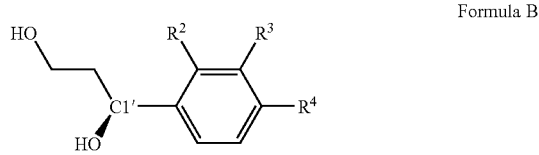

Formula B

The chiral center at the carbon, C1', has been established in this process step and the ratio of enantiomers was conserved throughout the remainder of the process.

2.0 Synthesis of PMEA:

Various preparations of PMEA and (R)-PMPA and their analogues are described in the literature (Arimilli et al, WO 99/04774; Schultze et al., *Tetrahedron Letters* 1998, 39, 1853–1856; Bischofberger et al., U.S. Pat. No. 5,514,798, U.S. Pat. No. 5,686,629; Holy et al., U.S. Pat. No. 4,659,825, U.S. Pat. No. 4,808,716, U.S. Pat. No. 5,130,427, U.S. Pat. No. 5,142,051) and are known to those skilled in the art. These procedures were modified for use herein and the modifications were unexpectedly found to eliminate both the time consuming isolation and purification steps given in the earlier literature. For the purpose of this invention the isolation of the diethyl ester of the phosphonic acid was not required to proceed to the next step. It was found that the ester could be deprotected without purification in this process.

In a typical method the adenine is reacted with a substituted or nonsubstituted ethylene carbonate and a base to generate 9-hydroxyethyladenine which was further alkylated with TsOCH$_2$P(O)OEt$_2$. The final step entailed a hydrolysis of the diethyl ester to generate PMEA, (R)-PMPA or their analogues.

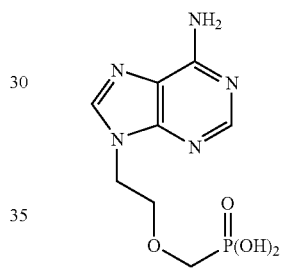

3. Synthesis of N6-protected PMEA-dichloridate:

In another step chlorination of PMEA is achieved using oxalyl chloride and N,N-diethylformamide to give N6 protected-PMEA-dichloridate. N,N-dialkylformamide used in the chlorination step not only forms a Vilsmeyer chlorinating agent, but also protects the NH$_2$ group at the 6 position. The protected chloridate intermediate was found to have favorable solubility properties that improved the overall yield and the diastereomeric ratio of the product. Use of other protecting groups such as acyl, alkoxycarbonyl, aryloxycarbonyl, and aralkyloxycarbonyl also enhance the solubility of the dichloridate and diastereomeric ratio of the expected product.

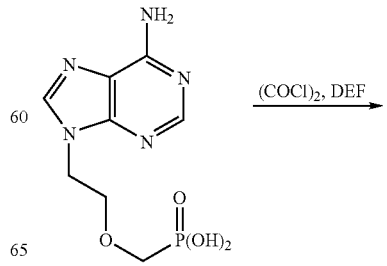

-continued

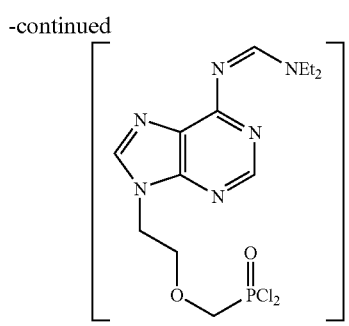

4. Coupling of Phosphonic Dichloridate and Chiral Diol:

Coupling of the protected parent phosphonic dichloridate and the chiral diol in the presence of a base resulted in a protected intermediate soluble in dichloromethane at lower temperatures.

4.1 Crystallization of cis Prodrug Salt:

Deprotection of the N6 position of the coupled phosphonic acid and chiral diol under mild acidic conditions and crystallization of the resultant product using methanesulfonic acid gave rise to the cis prodrug as a mesylate salt (Formula C) with 92–93% chemical purity. The trans isomer is the major impurity and a second crystallization of the final material from an alcohol such as methanol gave greater than 96% diastereomeric purity.

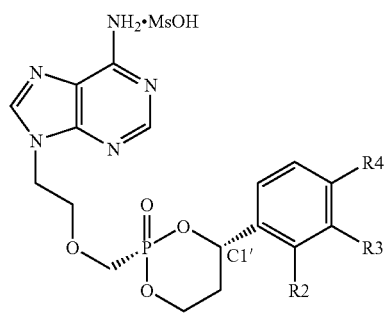

Formula C

The use of other acids including but not limited to such as sulfuric, nitric, hydrochloric, phosphoric, sulfonic, tartaric, citric, maleic, malic, malonic, lactic, oxalic acids and the like, may lead to better recovery and isomeric ratio of the product. The protocol as described for PMEA is also applicable to other PME or PMP derivatives.

4.2 Synthesis of 9-{2-[2,4-cis-(S)-(+)-4-(halophenyl)-2-oxo-1,3,2-dioxa-phosphorinan-2-yl]methoxyethyl}adenine mesylate:

The 9-{2-[2,4-cis-(S)-(+)-4-(halophenyl)-2-oxo-1,3,2-dioxaphosphorinan-2-yl]methoxyethyl}adenine mesylate (Formula C) was prepared via an eight step convergent synthetic sequence starting with adenine and halobenzoyl chloride. The final resultant compound (Formula C) contained two stereocenters: (1) the methine carbon (C1'); and (2) the phosphorus of the cyclic phosphonate ring. The stereochemistry at the carbon (C1') resulted from the chiral reduction of the intermediate ketoacid and the phosphorus chirality was the result of the diastereoselective coupling of the parent phosphonic acid and the chiral diol. The desired cis isomer, wherein cis refers to the isomeric relationship between the phosphorus-carbon bond and the carbon-phenyl bond of the cyclic phosphonate ring, was isolated via a selective crystallization of the methanesulfonic acid salt.

The starting materials of the chiral diol and the parent phosphonic acid were synthesized using modified procedures. The chiral diol was synthesized from 3-chlorobenzoyl chloride via a three step sequence and the parent phosphonic acid was synthesized from adenine via a four step sequence.

The final desired (cis) stereoisomer product is obtained with high purity via a novel coupling step wherein the parent phosphonic acid and the chiral diol were coupled to produce the final stereoisomer product.

Previous coupling efforts wherein PMEA was reacted with racemic diol using dehydrating agents such as, N,N'-dicyclohexylcarbodiimide and PyBOP in DMF/pyridine solvent systems, were found to require elevated temperatures (at least 100° C.) to achieve complete coupling. These reactions proceeded with a relatively minor diastereomeric excess (5–10% of the desired cis isomer). Unexpectedly and surprisingly, improved d.e.'s were noted when the reaction temperature was lowered. This aspect of the invention led to an effort to activate PMEA as the dichloridate, a more reactive chemical species. It was the inventors' desire to react the dichloridate of PMEA with the diol at lower temperatures. The dichloridate of PMEA is readily prepared using standard chlorination conditions. The coupling reaction with the dichloridate at low temperature was complicated by the poor solubility of the dichloridate. Accordingly, the inventors sought protecting groups of N6 that would aid in the solubilization of the dichloridate. One preferred protecting group was the N-(dialkylaminomethyleneimine).

Formation of the N-(dialkylaminomethyleneimine)-protected PMEA dichloridate was achieved by treatment of PMEA in the presence of a dialkylformamide, such as, dimethylformamide, diethylformamide, dibutylformamide, N-formylpiperidine, or N-formylmorpholine, with oxalyl chloride in refluxing dichloromethane.

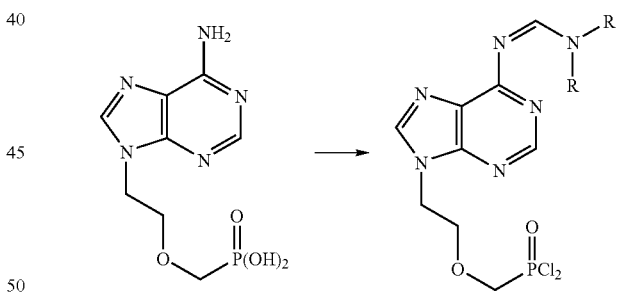

5.0 Effect of Dichloridate Addition Order and Temperature:

The higher order formamides (diethyl and higher) gave a more lipophilic nature to the dichloridate. This lipophilic nature was found to make the dichloridate more soluble in dichloromethane (DCM). The addition of the racemic diol to the dichloridate intermediate, in the presence of an excess of triethylamine (TEA), gave complete reaction but the reaction was found to have only a modest d.e. In a preferred embodiment, when the reagents were added in reverse order (i.e. the dichloridate was added to the diol/base mixture), an improved d.e. was obtained (cis:trans=71:29). Surprisingly the inventors found that the order of the addition and a low temperature produced a method for enriching the d.e. in favor of the cis isomer. The results are given in Table 1 (see entries 1–3).

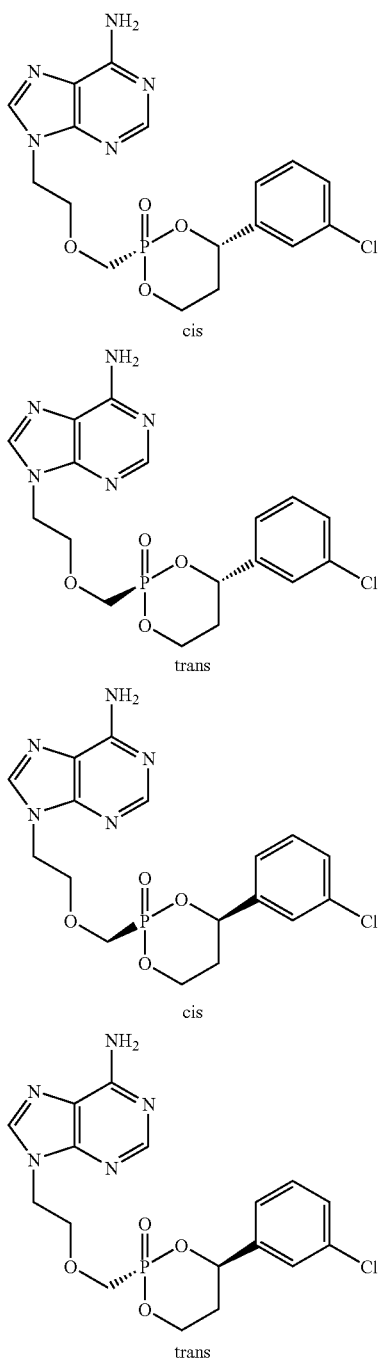

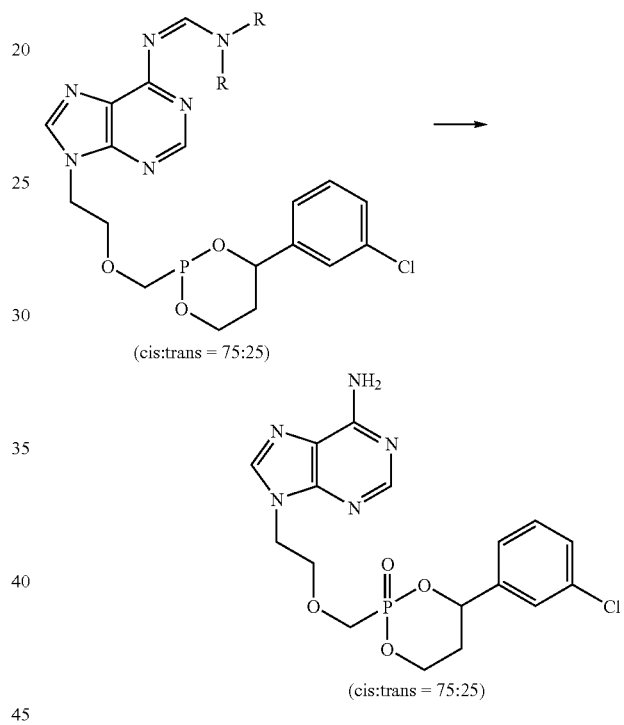

(cis:trans = 75:25)

(cis:trans = 75:25)

Table 1 also shows that superior cis-trans ratios are achieved by lowering the temperature of the coupling reaction. See entries (1–3).

With the unexpected advantage of dichloridate being added to the diol, it was preferable for the dichloridate to remain in solution for transferring. When R of the protecting group was methyl, the resulting dichloridate remained a slurry. Surprisingly, it was found that with an addition of a slight excess of pyridine (1.1 equivalents), the dichloridate slurry dissolved. This may be due to the neutralization of one equivalent of HCl and the resulting greater solubility of the free base dichloridate versus the dichloridate hydrochloride.

The resulting crude reaction mixture was subjected to a water/dichloromethane partition work-up and the isolated coupling mixture was treated with refluxing acetic acid in ethanol to effect nitrogen deprotection.

5.1 cis Isomer Salt Formation and Solvents:

When the coupling/deprotection sequence was performed with the chiral diol (S or R), the same d.e. was observed (50%), and it was discovered that the cis enantiomer did not crystallize from the reaction solution as did the cis racemate. Surprisingly, formation of certain salts of the 75:25 cis:trans mixture led to a crystallization of the desired cis diastereomer. A list of some salts that were used and the d.e.'s that were found of the solid and filtrates are listed in Table 2.

TABLE 1

EFFECT OF TEMPERATURE AND ADDITION ORDER

| Entry | R Group | Solvent | Temp (° C.) | Addition | cis:trans |
|---|---|---|---|---|---|
| 1 | Methyl | DCM | −70 | Dichloridate to diol | 75:25 |
| 2 | Methyl | DCM | −50 | Dichloridate to diol | 71:29 |
| 3 | Methyl | DCM | 0 | Dichlordate to diol | 63:36 |
| 4 | Methyl | DCM | −50 | Diol to dichloridate | 57:42 |
| 5 | Ethyl | DCM | −50 | Base to mixture | 66:34 |

TABLE 2 cis ISOMER SALT AND CRYSTALLIZATION SOLVENTS

| SALT | SOLVENT | SOLID (cis:trans) | FILTRATE (cis:trans) |
|---|---|---|---|
| Free base | | 75:25 | |
| Succinic acid | Ethanol | 82:18 | 70:30 |
| L-Tartaric acid | Ethanol | 70:30 | 85:15 |
| D-Tartaric acid | Ethanol | 76:24 | 77:23 |
| Maleic acid | Ethanol | 66:31 | 88:12 |

TABLE 2-continued cis ISOMER SALT AND CRYSTALLIZATION SOLVENTS

| SALT | SOLVENT | SOLID (cis:trans) | FILTRATE (cis:trans) |
|---|---|---|---|
| Methanesulfonic acid | Ethanol:acetone | 93:7 | 57:43 |
| L-Malic acid | Ethanol:acetone | 56:43 | 93:6 |
| D-Malic acid | Ethanol:acetone | 56:43 | 95:2 |

It was found that the methanesulfonic acid salt of the 75:25 cis:trans mixture gave the highest enrichment of the desired cis diastereomer (93:7). Deprotection was conducted by refluxing with a weak acid, such as acetic acid in an alcoholic solvent, e.g., ethanol. Methanesulfonic acid was then added to the reaction solution after deprotection was complete. At this stage it was found that the methanesulfonic acid selectively crystallized the desired cis diastereomer. The crude mesylate salt typically contained only 5–7% of the trans isomer, and a final recrystallization was developed to further decrease the trans levels to 1–3%. Table 3 lists some of the recrystallization solvent systems tried.

Using a sample containing 4% trans isomer dissolved in the solvents listed below, the cis isomer was enriched.

TABLE 3

FINAL RECRYSTALLIZATION SOLVENTS

| Solvent | *Volume (mL)/g | % Recovery | A % Trans |
|---|---|---|---|
| Methanol | 2.5 | 71.8 | 1.0 |
| Ethanol | 10.5 | 86.4 | 1.6 |
| Isopropanol | 48 | 88.4 | 2.2 |
| Methanol/Toluene (1/1) | 5.0 | 58.8 | 1.0 |
| Methanol/Isopropanol (1/1) | 4.0 | 85.0 | 2.0 |
| Methanol/Isopropanol (2/5) | 7.0 | 89.2 | 2.5 |
| Methanol/Ethanol (2/5) | 7.0 | 83.4 | 2.7 |
| Methanol/Acetone (1/1) | 4.0 | 73.2 | 1.2 |

*Volume used is per gram of sample.

The compounds used in this invention and their preparation can be understood further by the examples which illustrate some of the processes by which these compounds are prepared. These examples should not however be construed as specifically limiting the invention and variations of the compounds, now known or later developed, are considered to fall within the scope of the present invention as hereinafter claimed.

EXAMPLES

Example 1

Preparation of 3-(3-Chlorophenyl)-3-oxo-propanoic acid (1)

A 12 L, 3-neck round bottom flask was equipped with a mechanical stirrer and addition funnel (2 L). The flask was flushed with nitrogen and charged with diisopropylamine (636 mL) and THF (1.80 L). The stirred contents were cooled to −20° C. n-Butyllithium (1.81 L of a 2.5 M solution in hexanes) was added slowly with stirring, and the temperature was maintained between −20 and −28° C. After the addition was complete (30 min), the addition funnel was rinsed with hexanes (30 mL) and the stirred solution was then cooled to −62° C. Trimethylsilyl acetate (300 g) was added slowly with stirring, maintaining the temperature at <−60° C. After the addition was complete (about 30 minutes), the solution was stirred at −60° C. for 15 minutes. 3-Chlorobenzoyl chloride (295 mL) was added slowly with stirring, maintaining the temperature at <−60° C. After the addition was complete (about 65 minutes), the cooling bath was removed and the reaction solution was stirred for approximately 1.25 hours, with gradual warming to 0° C. The reaction flask was cooled with an ice bath, then water (1.8 L) was added to the stirred solution. The reaction mixture was stirred for 10 minutes, and then diluted with t-butyl methyl ether (MTBE) (1.0 L). The lower aqueous phase was separated and transferred to a round bottom flask equipped with a mechanical stirrer. MTBE was added (1.8 L) and the stirred mixture was cooled to <10° C. in an ice bath. Concentrated HCl solution (300 mL of 12 M solution) was added and the mixture was vigorously stirred. The layers were separated and aqueous phase was further acidified with concentrated HCl (30 mL) and extracted again with MTBE (1.0 L). The combined MTBE extracts were washed with approximately 10% NaCl solution (1 L), dried ($MgSO_4$, 70 g), filtered and concentrated under reduced pressure to give 827 g of a yellow solid. The crude solid was slurried in hexanes (2.2 L) and transferred to a round bottom flask equipped with a mechanical stirrer. The mixture was stirred at <10° C. for 1 hour, then filtered, washed with hexanes (4×100 mL) and dried to constant weight (−30 in. Hg, ambient temperature, 14 hours). The $^1$H-NMR analysis for this example and all following examples were performed on a VARIAN GEMINI-200 MHz Spectrometer. The samples were dissolved in the indicated solvent and the chemical shifts are referenced to the residual solvent.

Recovery=309 g

Pale yellow powder 1 (68.6%).

$^1$H-NMR (acetone-$d_6$): δ=4.1 (s, 2H), 7.5–8.1 (m, 4H)

Example 2

Preparation of (S)-3-(3-Chlorophenyl)-3-hydroxypropanoic acid (2)

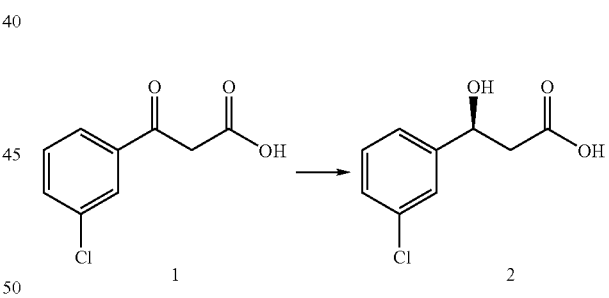

A 12 L, 3-neck round bottom flask was equipped with a mechanical stirrer and addition funnel (1 L). The flask was flushed with nitrogen and charged with 3-(3-chlorophenyl)-3-oxo-propanoic acid (275.5 g) 1 and dichloromethane (2.2 L). A thermocouple probe was immersed in the reaction slurry and the stirred contents were cooled to −20° C. Triethylamine (211 mL) was added over 5 minutes to the stirred slurry and all solids dissolved. A dichloromethane solution of (−)-B-chlorodiisopinocampheylborane (1.60 M, 1.04 L) was charged to the addition funnel, and then added slowly with stirring while maintaining the temperature between −20 and −25° C. After the addition was complete (approximately 35 min), the solution was warmed to ice bath temperature (2–3° C.) and stirred. After approximately 4 hours of stirring an in-process NMR analysis indicated the starting material 1 was <4%.

The residual starting material 1 was measured by proton NMR as follows: removing a 0.5 mL sample of the reaction mixture and quenching with water (0.5 mL) and 3 M NaOH solution (0.5 mL). The quenched mixture was stirred and the layers separated. The aqueous phase was acidified with 2 M HCl (1 mL) and extracted with ethyl acetate (1 mL). The organic phase was separated, filtered through a plug of $MgSO_4$ and concentrated with a stream of nitrogen. The residue was dissolved in $CH_2Cl_2$ and the solvent was evaporated with a stream of nitrogen. This residue was dissolved in acetone-$d_6$ and an analysis was done by $^1$H-NMR(acetone-$d_6$).

Water (1.2 L) was added to the cloudy orange reaction mixture, followed by 3 M NaOH solution (1.44 L). The mixture was vigorously stirred for 5 minutes and then transferred to a separatory funnel. The layers were separated and the basic aqueous phase was washed with ethyl acetate (1 L). The aqueous phase was acidified with concentrated HCl (300 mL) and extracted with ethyl acetate (2 times with 1.3 L each). The two acidic ethyl acetate extracts were combined, washed with approximately 10% NaCl solution (600 mL), dried with $MgSO_4$ (130 g), filtered and concentrated under reduced pressure to provide 328 g of a yellow oil. The oil crystallized upon standing. The resulting solid was slurried in ethyl acetate (180 mL) and transferred to a 2 L, 3-neck round bottom flask, equipped with a mechanical stirrer. The stirred ethyl acetate mixture was cooled to <10° C. (ice bath), then diluted with hexanes (800 mL). The resulting mixture was stirred at ice bath temperature for 4 h, and then filtered. The collected solid was washed with 4:1 hexanes:ethyl acetate (3×50 mL) and dried to constant weight (−30 inches of Hg, ambient temperature, 12 h).

Recovery=207.5 g

White powder 2 (74.5%)

$^1$H-NMR(acetone-$d_6$): δ=2.7 (d, J=6 Hz, 2H), 4.7 (d, J=4 Hz, 1H), 5.1–5.2 (m, 1H), 7.2–7.5 (m, 4H).

Example 3

Preparation of (S)-(−)-1-(3-Chlorophenyl)-1,3-propanediol (3)

A 12 L, 3-neck round bottom flask was equipped with a mechanical stirrer, addition funnel (2 L) and thermometer. The flask was flushed with nitrogen and charged with (S)-3-(3-chlorophenyl)-3-hydroxypropanoic acid 2 (206.7 g) and THF (850 mL), and the stirred solution was cooled to 5° C. (ice bath). A 1 M borane in THF solution (2.14 L) was charged to the addition funnel, and then added slowly with stirring maintaining the temperature at <10° C. After the addition was complete (approximately 1 hour), the cooling bath was removed and the solution was stirred at ambient temperature for 1 hour. The reaction solution was slowly and cautiously quenched with water (600 mL), followed by 3 M NaOH solution (850 mL). The mixture was stirred for 10 minutes with an observed temperature increase to approximately 40° C., and then the mixture was transferred to a separatory funnel. The layers were separated and the aqueous phase was extracted again with ethyl acetate (600 mL). The combined organic phase was washed with approximately 10% NaCl solution (500 mL), dried ($MgSO_4$, 322 g), filtered and concentrated under reduced pressure to provide 189.0 g of a pale yellow oil (101%). Preliminary analysis of the oil was by $^1$H-NMR ($CDCl_3$).

The oil was purified by vacuum distillation and the fraction at 125–155° C./0.15 mmHg was collected.

Recovery=180.9 g

Colorless oil 3 (94.0%).

$^1$H-NMR ($CDCl_3$): δ=2.9–3.1 (m, 2H), 2.5 (bs, 2H), 3.9 (t, J=5 Hz, 2H), 4.9 (dd, J=7.4, 4.8 Hz, 1H), 7.2–7.4 (m, 4H).

Procedure for ee Determination

For the chiral HPLC analysis the diol 3 was derivatized to the diacetate as follows:

The resultant diol 3 (5.0 mg, 0.026 mmol) was dissolved in dichloromethane (2.0 mL). Acetic anhydride (15 μL, 0.15 mmol) and 4-(dimethylamino)pyridine (13 mg, 0.10 mmol) were added and the solution was stirred at ambient temperature for 15 minutes. The reaction solution was quenched with 1 M HCl solution (3 mL) and the lower organic phase was separated, passed through a plug of $MgSO_4$, and concentrated with a stream of nitrogen. The residue was dissolved in methanol (1 mL) and analyzed by chiral HPLC. Surprisingly, the ee for the diol 3 was determined to be >98%.

HPLC conditions:

Column: Pirkle covalent (S,S) Whelk-O 10/100 krom FEC, 250×4.6 mm; mobile phase=70:30, methanol:water, isocratic; flow rate=1.5 mL/min; injection volume=10 μL UV detection at 220 nm.

Retention times: S-diol (diacetate)=12.1 min, R-diol (diacetate)=8.6 min.

Example 4

Preparation of Diethyl p-toluenesulfonyloxymethylphosphonate (4)

A 12 L, 3-neck round bottom flask was equipped with a mechanical stirrer, condenser, thermometer and heating mantle. The flask was flushed with nitrogen and charged with diethyl phosphite (554 g), paraformaldehyde (142 g), toluene (2 L) and triethylamine (53 mL). The mixture was stirred at 85–90° C. for 2 hours, and then refluxed for 1 hour. The resulting yellow solution was cooled to 4° C. in an ice bath and p-toluenesulfonyl chloride (718 g) was added. The condenser was replaced with an addition funnel and triethylamine (750 mL) was added slowly with stirring, maintaining the temperature at <10° C. After the addition was complete (45 minutes), the resulting mixture was stirred at ambient temperature for 14 hours. The mixture was filtered and the filtercake was washed with toluene (2×250 mL). The combined filtrate and washings were washed with water (2×1 L), dried ($MgSO_4$, 200 g), filtered through diatomaceous earth (Celite 521, CAS 61790-53-2), and concentrated under reduced pressure.

Recovery=1004 g.

Cloudy yellow oil 4 (77.6%).

$^1$H-NMR ($CDCl_3$). Δ=1.3 (t, J=8H, m, 3H), 2.4 (s, 3H), 4.0–4.2 (m, 4H), 7.2 (d, J=8 Hz, 2H), 7.8 (d, J=8 Hz, 2H).

Example 5

Preparation of 9-(2-Hydroxyethyl)adenine (5)

A 12 L, 3-necked round bottom flask was equipped with a mechanical stirrer, condenser, thermometer and heating mantle. The flask was flushed with nitrogen and charged with adenine (504 g), ethylene carbonate (343 g), DMF (3.7 L) and sodium hydroxide (7.80 g). The stirred mixture was heated to reflux (approximately 80 minutes to reach reflux, pot temperature=145° C.), and then refluxed for 2 hours. The heating mantle was removed and the yellow solution was cooled to below 100° C. The resulting mixture was then cooled to 5° C. in an ice bath and diluted with toluene (3.8 L). The resulting mixture was stirred at <10° C. for 2 hours and then filtered. The collected solid was washed with toluene (2×0.5) and cold ethanol (1.5 L), then dried to constant weight (–30 in. Hg, 50° C., 14 h).

The solid 5 was analyzed by HPLC and $^1$H-NMR (DMSO-$d_6$).

HPLC conditions:

Silica column (particle size, 10 microns)(Phenomenex Bondclone) 10 C18 column, 300×3.9 mm; Mobile phase: Solvent A=20 mM potassium phosphate, pH 6.2; Solvent B=acetonitrile; Gradient: 0–60% B/15 min.,60–0% B/2 min., 0% B/3 min.; UV detection at 270 nm.

Retention times: Product=6.5 min., 3-regioisomer (tentative)=5.6 min.

Recovery=624 g.

Pale yellow solid 5 (93.3%).

$^1$H-NMR (DMSO-$d_6$): δ=3.6–3.8 (m, 2H), 4.1 (t, J=6 Hz, 2H), 5.0 (bs, 1H), 7.2 (bs, 2H), 8.05 (s, 1H), 8.10 (s, 1H).

Example 6

Preparation of
9-(2-Diethylphosphonylmethoxyethyl)adenine (6)

A 5 L, 3-neck round bottom flask was equipped with a mechanical stirrer and thermometer. The flask was flushed with nitrogen and charged with 9-(2-hydroxyethyl)adenine 5 (464 g) and DMF (1.40 L). The stirred slurry was cooled to 10° C. in an ice bath and sodium tert-butoxide (436 g) was added in one portion with a corresponding increase in temperature to 29° C. The ice bath was removed and the mixture was stirred at ambient temperature for 1 hour yielding a slightly cloudy solution. The reaction flask was equipped with an addition funnel (2 L) and the stirred contents were cooled to 5° C. (ice bath). Diethyl p-toluenesulfonyloxymethylphosphonate (1130 g), as a solution in DMF (700 mL), was added slowly with stirring, maintaining the temperature at <10° C. After the addition was complete (2 hours), the cooling bath was removed and the mixture was stirred at ambient temperature for 1 hour. HPLC was used to determine completeness of the reaction. The mixture was sampled by removing 0.05 mL of the reaction mixture and dissolving the material in 10 mL of 20 mM potassium phosphate buffer, pH 6.2.

HPLC conditions:

Silica column (particle size,10 microns)(Phenomenex Bondclone) 10 C18 column, 300×3.9 mm; Mobile phase: Solvent A=20 mM potassium phosphate (, pH 6.2, Solvent B=acetonitrile; Gradient: 0–60% B/15 min., 60–0% B/2 min., 0% B/3 min.; UV detection at 270 nm; Injection volume=10 uL.

Retention times: Product 6=9.2 minutes, Starting material 5=6.5 minutes.

The stirred mixture was cooled to 10° C. and 80% acetic acid (250 mL) was slowly added. After the addition was complete (approximately 15 minutes), the mixture was stirred at ambient temperature for 30 minutes and the temperature gradually increased to 30° C. The solvent was evaporated under reduced pressure (R-152 rotary evaporator, 5 mm Hg) to provide 2115 g of an orange sludge. The material was used without purification for the next step.

Example 7

Preparation of
9-(2-Phosphonylmethoxyethyl)adenine (7)

A 12 L, 3-neck round bottom flask was equipped with a mechanical stirrer. The flask was charged with the crude 9-(2-diethylphosphonylmethoxyethyl)adenine 6, as a slurry in acetonitrile (4.0 L). The mixture was stirred at ambient temperature for 30 minutes and then filtered. The filter cake was washed with acetonitrile (2×0.5 L) and the combined filtrate and washings were used directly as follows.

A 22 L, 3-neck round bottom flask was equipped with a mechanical stirrer, thermometer, condenser and heating mantle. The flask was flushed with nitrogen and charged with the 9-(2-diethylphosphonylmethoxyethyl)adenine 6 solution (2.59 mol), chlorotrimethylsilane (1.315 L) and potassium iodide (1.719 kg). There was a gradual increase in temperature after the addition of KI to 35° C. The stirred mixture was then heated to 55° C. and stirred at 50–55° C. for 1 hour. The mixture was stirred for an additional 3 hours with gradual cooling to 38° C. HPLC was used to determine completeness of the reaction.

HPLC conditions:

Silica column (particle size, 10 microns)(Phenomenex Bondclone) 10 C18, 300×3.9 mm column; mobile phase: Solvent A=20 mM potassium phosphate, pH 6.2, Solvent B=acetonitrile; Gradient: 0–60% B/15 min., 60–0% B/2 min., 0% B/3 min.; UV detection at 270 nm.

Retention times: Product 7=5.2 min., starting material 6=9.2 min.

The reaction flask was equipped with an addition funnel (2 L) and 3.5 M NaOH solution (4 L) was slowly added with a temperature increase from 32 to 44° C. The two liquid phase system was transferred to a 5 gal. stationary separatory funnel and the layers were separated. The basic aqueous phase was extracted with ethyl acetate (2 L) and then transferred to a 12 L, 3-neck flask, equipped with a mechanical stirrer and an addition funnel (1 L). Concentrated HCl was added slowly with stirring until the pH was 3.0 as determined by standard laboratory pH meter. The resulting yellow solution was stirred at ambient temperature for 12 hours. A precipitate formed. The stirred mixture was cooled to 7° C. in an ice bath and the pH was readjusted to 3.0 with concentrated HCl. The mixture was stirred at ice bath temperature for 5 hours and then filtered. Filtration took approximately 4 hours. The collected solid was washed with acetone and air dried on the filter funnel.

A 5 L, 3-neck round bottom flask was equipped with a mechanical stirrer and a 250 mL addition funnel. The flask was charged with the crude solid and 1 M sodium hydroxide solution (1.25 L). The mixture was stirred until all solids were dissolved (15 minutes). Concentrated HCl solution was added slowly to the stirred solution until the pH was 3.0. The resulting mixture was stirred at ambient temperature for 4 hours and then filtered. The collected solid was washed with water (2×250 mL) and acetone (200 mL), and dried to constant weight (–30 in. Hg, 60° C., 14 hours).

Recovery=292 g

Off-white solid (41.3%).

$^1$H-NMR ($D_2O$); δ=3.25 (d, J=8 Hz, 2H), 3.70 (t, J=4 Hz, 2H), 4.10 (t, J=4 Hz, 2H), 4.60 (s, 4H), 7.80 (s, 1H), 7.90 (s, 1H).

Example 8

Preparation 9-{2-[2,4-cis(S)-(+)-4-(3-Chlorophenyl)-2-oxo-1,3,2-dioxaphosphorinan-2-yl]methoxyethyl}adenine methanesulfonate (9)

Example 8.1

Formation of Dichloridate (8)

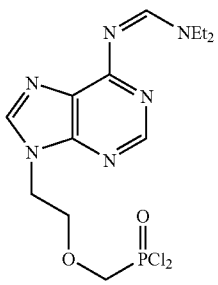

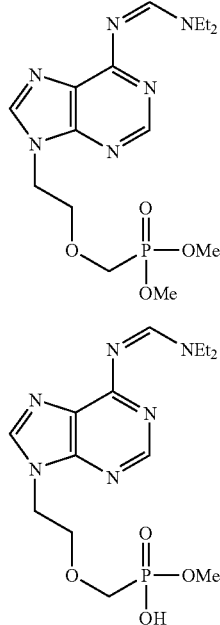

A 2 L, 3-neck round bottom flask was equipped with a mechanical stirrer, condenser, addition funnel (125 mL) and heating mantle. The flask was flushed with nitrogen and charged with PMEA 7 (50.0 g), dichloromethane (650 mL) and N,N-diethylformamide (22.5 mL). Oxalyl chloride (58.0 mL) was charged to the addition funnel, and added slowly to the stirred reaction mixture. Vigorous gas evolution occurred and the nitrogen inlet was removed to facilitate the gas to escape. After the addition was complete (15 minutes), the addition funnel was removed and the vigorously stirred mixture was heated at reflux for 2 hours. The solution remained a slurry during this process. The reaction mixture was cooled slightly, and additional oxalyl chloride (1.0 mL) and N,N-diethylformamide (0.4 ml) were added. The addition of N,N-diethylformamide produced vigorous gas evolution. The resulting mixture was heated at reflux until all solids were dissolved (additional 2.5 hours, total reaction time was approximately 4.5 hours). HPLC analysis of the reaction solution indicated the product 8 at 83 Area %. The reaction was monitored for formation of the dichloiidate. A sample of the reaction mixture (approximately 50 µL) was removed and quenched in anhydrous methanol (1 mL) containing 1 drop of triethylamine. The resulting methyl phosphonate(s) were analyzed by HPLC.

HPLC conditions:
YMC-Pack R & D, R-33-5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 µL; UV detection at 270 nm.

Retention times: Dimethylphosphonate 11=8.5 min., monomethyl phosphonate 12=5.8 min.

The reaction solution was cooled slightly and the condenser was replaced with a distillation head with thermometer, condenser and collection flask (250 mL). The reaction solution was heated to reflux and 250 mL of distillate was collected. The pot solution was diluted with dichloromethane (250 mL) and an additional 250 mL of distillate was collected. The distillation head was removed and the reaction flask was placed under nitrogen. The solution was diluted with dichloromethane (100 mL) and cooled to ice bath temperature. HPLC analysis of the reaction solution indicated the product at 89 Area %.

HPLC conditions:
YMC-Pack R & D, R-33-5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. Vol=10 µL; UV detection at 270 nm.

Retention times: Product 8=8.5 min., starting material 7=5.9 min

Pyridine (18 mL) was added slowly to the stirred solution. After the addition was complete (5 minutes), the resulting pale orange solution was stored at ice bath temperature until used (30 minutes).

Example 8.2

Coupling Reaction

A 2 L, 3-neck round bottom flask was equipped with a mechanical stirrer, and addition funnel (1 L). The flask was flushed with nitrogen and charged with (S)-(−)-(3-chlorophenyl)-1,3-propanediol 3 (34.1 g), as a solution in dichloromethane (500 mL) and triethylamine (125 ml). A thermocouple probe was immersed in the reaction solution and the stirred contents were cooled to −71° C. (dry ice/isopropanol). The dichloridate solution 8 was charged to the addition funnel, then added slowly with stirring, maintaining the temperature <−67° C. After the addition was complete (1.25 h), the cooling bath was removed and the stirred mixture was warmed to 0° C. over 30 min. The reaction mixture was washed with water (550 mL) and the layers were separated. The dichloromethane phase was diluted with ethyl acetate (500 mL) and washed with 5% NaCl solution (600 mL). The organic phase was dried (MgSO₄, 50 g), filtered through diatomaceous earth (Celite 521), and concentrated under reduced pressure to provide 108 g of a dark red sludge. The sample was dissolved in methanol.

HPLC conditions:

YMC-Pack R & D, R-33-5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 μL; UV detection at 270 nm.

Retention times: cis 13=12.5 min., trans 14=13.0 min.

13

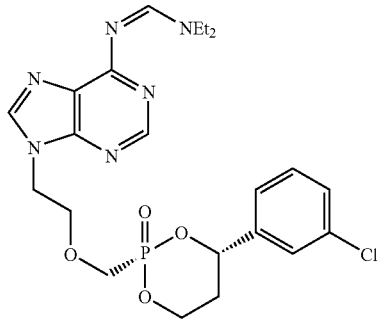

14

The material was dissolved in ethanol (500 mL) and transferred to a 2 L round bottom flask equipped with magnetic stirring, condenser and heating mantle. Acetic acid (55 mL) was added and the red solution was heated at reflux for 8 hours. HPLC indicated the reaction was complete. The sample was dissolved in methanol.

HPLC conditions:

YMC-Pack R & D, R-33-5 S-5 120A, 250×4.6 mm; mobile phase: Solvent A=20 mM potassium phosphate, pH 6.2; Solvent B=acetonitrile; gradient: 10–60% B/15 min., 60–10% B/2 min., 10% B/3 min.; 1.4 mL/min.; inj. vol.=10 μL; UV detection at 270 nm. 6.

Retention times: cis 15=9.5 min., trans. 16=9.8 min.

15

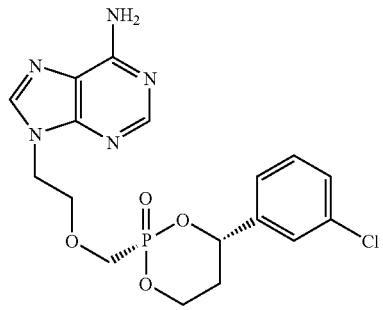

16

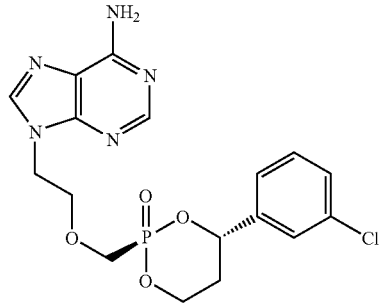

Example 8.3

Crystallization of 9-{2-[2,4-cis(S)-(+)-4-(3-Chlorophenyl)-2-oxo-1,3,2-dioxaphosphorinan-2-yl] methoxyethyl}adenine methanesulfonate (9)

Methanesulfonic acid (21.5 mL) was added and a precipitate formed after 15 min. The mixture was diluted with ethanol (400 mL) and heated until all solids dissolved (pot temperature=70° C.). The solution was cooled with stirring and a precipitate formed at 46° C. The resulting mixture was stirred for 2 h, with cooling to ambient temperature, then at ice bath temperature for 2.5 h. The mixture was filtered and the collected solid was washed with ethanol (2×15 mL) and dried to constant weight (−30 in. Hg, 55° C., 14 h). Recovery=49.4 g of a white powder 9 (51.9%). The solid contained 6.5 Area % of the trans diastereomer.

Chiral HPLC: Pirkle covalent (S,S) Whelk-O 1 10/100 krom FEC 250×4.6 mm; mobile phase=55:45, methanol: 0.1% HOAc in water; isocratic; 1.0 mL/min.; inj. Vol.=10 μL; UV detection at 260 nm; sample preparation=2.0 mg/mL in water. Retention times: cis-(R) 5=24.6 min., trans-(R) 6=27.5 min., cis-(S) 7=18.0 min.

¹H-NMR (D₂O) was used to confirm structure of components.

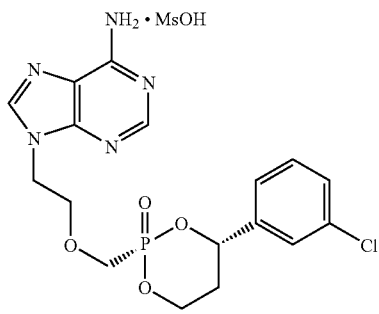

Example 8.4

Recrystallization of 9-{2-[2,4-cis-(S)-(+)-4-(3-Chlorophenyl)-2-oxo-1,3,2-dioxaphosphorinan-2-yl]methoxyethyl}adenine methanesulfonate (9)

A 3 L, 3-neck round bottom flask was equipped with a mechanical stirrer, condenser, heating mantle and thermometer. The flask was charged with 2 batches of crude mesylate salt 9 and ethanol (1.4 L). The stirred mixture was heated at reflux (pot temperature was 78° C.) until all solids dissolved (approximately 10 minutes). The stirred mixture was gradually cooled to ambient temperature over 1.5 hours (a precipitate formed at 56° C.). The mixture was stirred at ambient temperature for an additional 2 hrs., then filtered. The collected solid was washed with ethanol (2×15mL) and dried to constant weight (–30 in Hg, 65° C., 60 hrs.).
Color: off white granular solid
Purity=97% (HPLC)
Optical purity (Chiral HPLC) >99.5%.
M.P.(° C.): 186.5–188
Specific Rotation (MeOH, 25° C., 589 nm): +16.429
Composition: C, 41.58; H, 4.56; N, 13.37 [Theoretical: C, 41.50; H, 4.53; N, 13.35]
$^1$H NMR ($D_2O$): δ=1.30–1.60 (m, 1H), 1.80–1.95 (m, 1H), 2.60 (s, 3H), 3.70–3.90 (m, 4H),4.10–4.50 (m, 2H), 4.60 (s, 3H), 5.15–5.40 (m, 1H), 6.70–6.80 (m, 2H), 7.00–7.10 (m, 2H), 8.00 (s, 1H), 8.10 (s, 1H).

Example 9

Formation of Hydrochloride Salt via Salt Exchange

In this instant invention the oxalate salt of the phosphonic acid based prodrugs was also formed. This salt form of the prodrug could be exchanged for other salts that are pharmaceutically acceptable. The oxalate salt is dissolved in a solution containing an acid with a higher $pK_a$, the acid dissociation constant.

A 3-neck round bottom flask is equipped with a mechanical stirrer, condenser, heating mantle and thermometer. The flask is charged with crude oxalate salt and ethanol (5–10% solution by weight). The stirred mixture is heated at reflux (pot temperature is 78° C.) until all solids dissolve. The solution is acidified with HCl and the stirred mixture is gradually cooled to ambient temperature (a precipitate forms as the temperature cools). The mixture is stirred at ambient temperature with filtration following. The collected solid consisting of the hydrochloride salt is washed with ethanol and is dried in a vacuum oven to constant weight (oven temperature=65° C.).

Example 10

Formation of the Sulfate Salt via Salt Exchange

A 3-neck round bottom flask is equipped with a mechanical stirrer, condenser, heating mantle and thermometer. The flask is charged with crude mesylate salt 9 and ethanol (5–10% solution by weight). The stirred mixture is heated at reflux (pot temperature is 78° C.) until all solids dissolve. The solution is acidified with sulfuric acid and the stirred mixture is gradually cooled to ambient temperature (a precipitate forms as the temperature decreases). The mixture is stirred at ambient temperature and filtration of desired product follows. The collected solid consisting of the sulfate salt is washed with ethanol and is dried in a vacuum oven to constant weight (oven temperature=65° C.).

Example 11

Formation of the Sulfate Salt via Free Base Reaction

A 3-neck round bottom flask is equipped with a mechanical stirrer, condenser, heating mantle and thermometer. The flask is charged with crude mesylate salt 9 and $NaHCO_3$ solution. The stirred mixture is heated until all solids dissolve. The solution is acidified with sulfuric acid and the stirred mixture is gradually cooled to ambient temperature (a precipitate forms as the temperature decreases). The mixture is stirred at ambient temperature followed by filtration. The collected solid consisting of the sulfate salt is washed with ethanol and is dried in a vacuum oven to constant weight (oven temperature=65° C.).

Example 12

Formation of the Maleate Salt via Anionic Resin Reaction

A 3-neck round bottom flask is equipped with a mechanical stirrer, condenser, heating mantle and thermometer. The flask is charged with crude mesylate salt 9. The stirred mixture is heated until all solids dissolve. The mixture containing the mesylate salt 9 is run through an anionic resin. The resultant solution containing the free base of the compound of Formula 1 is acidified with maleic acid and the stirred mixture is gradually cooled to ambient temperature (a precipitate forms as the temperature decreases). The mixture is stirred at ambient temperature followed by filtration. The collected solid consisting of the maleate salt is washed with ethanol and is dried in a vacuum oven to constant weight (oven temperature=65° C.).

We claim:

1. A method for the preparation of a compound of Formula I:

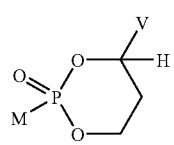

Formula I comprising:
(a) coupling 1-arylpropane-1,3-diol, wherein the aryl is a phenyl optionally substituted with 1–2 substituents selected from the group consisting of fluoro, chloro, and bromo, with MPOCl$_2$ substituted at the N-6 position with a nitrogen protecting group; and
(b) removing the N-6 protecting group;
wherein:
M and V are cis to one another, MPO$_3$H$_2$ is a phosphonic acid selected from the group consisting of 9-(2-phosphonylmethoxyethyl)adenine and (R)-9-(2-phosphonylmethoxypropyl)adenine; and V is phenyl, optionally substituted with 1–2 substituents selected from the group consisting of fluoro, chloro, and bromo.

2. The method of claim 1 wherein the cis isomer is present at an excess of at least 50% compared to the corresponding trans isomer.

3. The method of claim 2 further comprising adding an acid to form an acid addition salt of the compound of Formula I.

4. The method of claim 3 wherein the acid is selected from the group consisting of HCl, HBr, acetic acid, citric acid, maleic acid, methanesulfonic acid, nitric acid, phosphoric acid, succinic acid, sulfuric acid, and tartaric acid.

5. The method of claim 3 wherein the acid is selected from the group consisting of methanesulfonic acid, succinic acid, citric acid, and oxalic acid.

6. The method of claim 5 wherein the acid is methanesulfonic acid.

7. The method of claim 3 further comprising crystallizing the acid addition salt.

8. The method of claim 7 wherein the solvent for crystallizing the acid addition salt is selected from the group consisting of methanol, ethanol, isopropanol, acetone, toluene, and mixtures thereof.

9. The method of claim 3 further comprising:
(a) reacting the acid addition salt of the compound of Formula I with a second acid that has a higher acid dissociation constant than the first acid, and
(b) crystallizing a second acid addition salt of the compound of Formula I.

10. The method of claim 3 further comprising:
(a) neutralizing the acid addition salt of the compound of Formula I,
(b) obtaining the free base of the compound of Formula I,
(c) adding a pharmaceutically acceptable acid, and
(d) crystallizing a second acid addition salt of the compound of Formula I.

11. The method of claim 3 further comprising:
(a) utilizing an anionic resin to obtain free base of the acid addition salt of the compound of Formula I,
(b) adding a pharmaceutically acceptable acid, and
(c) crystallizing a second acid addition salt of the compound of Formula I.

12. The method of claim 1 wherein the temperature for the coupling step is at or below −50° C.

13. The method in claim 12 wherein the temperature for the coupling step is at or below −70° C.

14. The method as recited in claim 1 wherein the MPOCl$_2$ is added to the 1-phenylpropane-1,3-diol.

15. The method of claim 1 wherein the MPOCl$_2$ is added to the 1-phenylpropane-1,3-diol at a temperature at or below −50° C.

16. The method of claim 1 further comprising addition of a base in (a).

17. The method of claim 1 wherein the N-6 protecting group forms a dialkylaminomethyleneimino group with a nitrogen atom at the N-6 position of the MPOCl$_2$.

18. The method of claim 17 wherein the N-6 protecting group is produced as part of a reaction to form the MPOCl$_2$.

19. The method of claim 17 wherein the dialkylaminomethyleneimino group is selected from the group consisting of a dimethylaminomethyleneimino group, a diethylaminomethyleneimino group, a dipropylaminomethyleneimino group, and a dibutylaminomethyleneimino group.

20. The method of claim 1 wherein the compound of Formula I has the stereochemistry of Formula II:

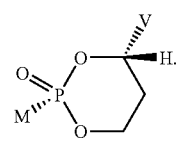

Formula II

21. The method of claim 20 wherein the temperature for the coupling step is at or below −50° C.

22. A method for the preparation of a compound of Formula I:

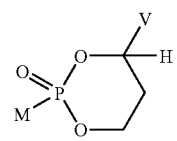

Formula I comprising:
(a) coupling a chiral 1-(3-chlorophenyl)propane-1,3-diol with MPOCl$_2$ substituted at the N-6 position with a nitrogen protecting group, and
(b) removing the N-6 protecting group; wherein:
M and V are cis to one another, MPO$_3$H$_2$ is a phosphonic acid selected from the group consisting of 9-(2-phosphonylmethoxyethyl)adenine and (R)-9-(2-phosphonylmethoxypropyl)adenine; and V is 3-chlorophenyl.

23. The method of claim 22 wherein the cis isomer is present at an excess of at least 50% compared to the corresponding trans isomer.

24. The method of claim 23 further comprising adding an acid to form an acid addition salt of Formula I.

25. The method of claim 24 wherein the acid is selected from the group consisting of methanesulfonic acid, succinic acid, citric acid, and oxalic acid.

26. The method of claim 25 wherein the acid is methanesulfonic acid.

27. The method of claim 22 wherein the temperature for the coupling step is at or below −50° C.

28. The method of claim 27 wherein the temperature for the coupling step is at or below −70° C.

29. The method of claim 22 wherein the MPOCl$_2$ is added to the chiral 1-(3-chlorophenyl)propane-1,3-diol.

30. The method of claim 22 wherein the compound of Formula I has the stereochemistry of Formula II:

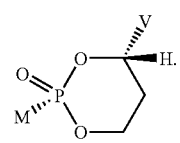

Formula II

31. The method of claim 30 wherein the temperature for the coupling step is at or below −50° C.

32. The method of claim 30 further comprising adding an acid to form an acid addition salt of Formula II.

33. The method of claim 32 wherein the acid is selected from the group consisting of methanesulfonic acid, succinic acid, citric acid, and oxalic acid.

34. The method of claim 33 wherein the acid is methanesulfonic acid.

35. The method of claim 24 further comprising crystallizing the acid addition salt from a solvent selected from the group consisting of methanol, ethanol, isopropanol, toluene, acetone, and mixtures thereof.

36. The method as recited in claim 22 wherein the N-6 protecting group forms a dialkylaminomethyleneimino group with a nitrogen atom at the N-6 position of the MPOCl$_2$.

37. The method as recited in claim 36 wherein the N-6 protecting group is produced as part of a reaction to form the MPOCl$_2$.

38. The method as recited in claim 36 wherein the dialkylaminomethyleneimino group is selected from the group consisting of a dimethylaminomethyleneimino group, a diethylaminomethyleneimino group, a dipropylaminomethyleneimino group, and a dibutylaminomethyleneimino group.

39. A method for the preparation of a compound of Formula I:

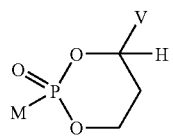

Formula I comprising:
(a) coupling a chiral 1-(2-bromophenyl)propane-1,3-diol with MPOCl$_2$ substituted at the N-6 position with a nitrogen protecting group; and
(b) removing the N-6 protecting group;
wherein:
M and V are cis to one another, MPO$_3$H$_2$ is phosphonic acid selected from the group consisting of 9-(2-phosphonylmethoxyethyl)adenine, and (R)-9-(2-phosphonylmethoxypropyl)adenine; and V is 2-bromophenyl.

40. The method of claim 39 wherein the cis isomer is present at an excess of at least 50% compared to the corresponding trans isomer.

41. The method of claim 40 further comprising adding an acid to form an acid addition salt of Formula I.

42. The method of claim 41 wherein the acid is selected from the group consisting of methanesulfonic acid, succinic acid, citric acid, and oxalic acid.

43. The method of claim 42 wherein the acid is methanesulfonic acid.

44. The method of claim 39 wherein the temperature for the coupling step is at or below −50° C.

45. The method of claim 44 wherein the temperature for the coupling step is at or below −70° C.

46. The method of claim 39 wherein the MPOCl$_2$ is added to the chiral 1-(2-bromophenyl)propane-1,3-diol.

47. The method of claim 39 wherein the compound of Formula I has the stereochemistry of Formula II:

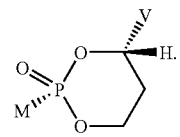

Formula II

48. The method of claim 40 wherein the temperature for the coupling step is at or below −50° C.

49. The method of claim 47 further comprising adding acid to form an acid addition salt of Formula II.

50. The method of claim 49 wherein the acid is selected from the group consisting of methanesulfonic acid, succinic acid, citric acid, and oxalic acid.

51. The method of claim 50 wherein the acid is methanesulfonic acid.

52. The method of claim 41 further comprising crystallization of the acid addition salt from a solvent selected from the group consisting of methanol, ethanol, isopropanol, acetone, toluene, and mixtures thereof.

53. The method of claim 39 wherein the N-6 protecting group forms a dialkylaminomethyleneimino group with a nitrogen atom at the N-6 position of the MPOCl$_2$.

54. The method of claim 53 wherein the N-6 protecting group is produced as part of a reaction to form the MPOCl$_2$.

55. The method of claim 53 wherein the dialkylaminomethyleneimino group is selected from the group consisting of a dimethylaminomethyleneimino group, a diethylaminomethyleneimino group, a dipropylaminomethyleneimino group, and a dibutylaminomethyleneimino group.

56. A method for the conversion of an acid addition salt compound of Formula I:

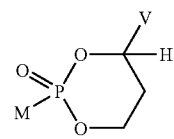

Formula I wherein:
M and V are cis to one another and MPO$_3$H$_2$ is a phosphonic acid selected from the group consisting of 9-(2-phosphonylmethoxyethyl)adenine, and (R)-9-(2-phosphonylmethoxypropyl)adenine; wherein V is phenyl, optionally substituted with 1–2 substituents selected from a group consisting of fluoro, chloro, and bromo; comprising:
(a) reacting said first acid addition salt compound of Formula I with a second acid that has a higher acid dissociation constant than the first acid, and
(b) crystallizing a second acid salt compound of Formula I.

57. The method of claim 56 wherein the second acid is selected from the group consisting of HCl, HBr, acetic acid, citric acid, maleic acid, methanesulfonic acid, nitric acid, phosphoric acid, succinic acid, sulfuric acid, and tartaric acid.

58. The method of claim 57 wherein the second acid is selected from the group consisting of methanesulfonic acid, succinic acid, citric acid, and oxalic acid.

59. The method of claim 58 wherein the second acid is methanesulfonic acid.

60. A method for the conversion of a first acid addition salt compound of Formula I:

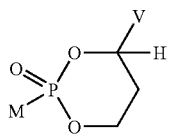

Formula I wherein:

M and V are cis to one another and $MPO_3H_2$ is a phosphonic acid selected from the group consisting of 9-(2-phosphonylmethoxyethyl)adenine, and (R)-9-(2-phosphonylmethoxypropyl)adenine; wherein V is phenyl, optionally substituted with 1–2 substituents selected from a group consisting of fluoro, chloro, and bromo; comprising:
(a) neutralizing said first acid addition salt compound of Formula I,
(b) obtaining the free base of the compound of Formula I,
(c) adding a pharmaceutically acceptable acid, and
(d) crystallizing a second acid salt compound of Formula I.

61. The method of claim 60 wherein the pharmaceutically acceptable acid is selected from the group consisting of HCl, HBr, acetic acid, citric acid, maleic acid, methanesulfonic acid, nitric acid, phosphoric acid, succinic acid, sulfuric acid, and tartaric acid.

62. A method for the conversion of a first acid addition salt compound of Formula I:

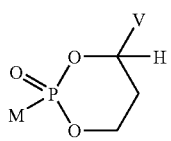

Formula I wherein:

M and V are cis to one another and $MPO_3H_2$ is a phosphonic acid selected from the group consisting of 9-(2-phosphonylmethoxyethyl)adenine, and (R)-9-(2-phosphonylmethoxypropyl)adenine; wherein V is phenyl, optionally substituted with 1–2 substituents selected from a group consisting of fluoro, chloro, and bromo; comprising:
(a) utilizing an anionic resin to obtain the free base of the compound of Formula I,
(b) adding a pharmaceutically acceptable acid, and
(c) crystallizing a second acid addition salt compound of Formula I.

63. The method of claim 62 wherein the pharmaceutically acceptable acid is selected from the group consisting of HCl, HBr, acetic acid, citric acid, maleic acid, methanesulfonic acid, nitric acid, phosphoric acid, succinic acid, sulfuric acid, and tartaric acid.

64. The method of claim 1, wherein the N-6 protecting group forms an N-piperidinomethyleneimino group, an N-morpholinomethyleneimino group, or an N-pyrrolidinomethyleneimino group with a nitrogen atom at the N-6 position of the $MPOCl_2$.

65. The method of claim 22, wherein the N-6 protecting group forms an N-piperidinomethyleneimino group, an N-morpholinomethyleneimino group, or an N-pyrrolidinomethyleneimino group with a nitrogen atom at the N-6 position of the $MPOCl_2$.

66. The method of claim 39, wherein the N-6 protecting group forms an N-piperidinomethyleneimino group, an N-morpholinomethyleneimino group, or an N-pyrrolidinomethyleneimino group with a nitrogen atom at the N-6 position of the $MPOCl_2$.

* * * * *